United States Patent

Stull et al.

[11] Patent Number: 6,025,133
[45] Date of Patent: Feb. 15, 2000

[54] PROMOTER-SEQUESTERED OLIGONUCLEOSIDE AND METHOD OF USE

[75] Inventors: Paul D. Stull; Kristi K. Myers; Michael M. Becker, all of San Diego, Calif.

[73] Assignee: Gen-Probe Incorporated, San Diego, Calif.

[21] Appl. No.: 08/770,941

[22] Filed: Dec. 30, 1996

[51] Int. Cl.[7] .............................. C12Q 1/68; C12P 19/34; C07H 21/04
[52] U.S. Cl. ......................... 435/6; 435/91.1; 435/91.2; 536/22.1; 536/24.3
[58] Field of Search .................. 536/22.1, 24.3; 435/91.2, 6, 91.1

[56] References Cited

U.S. PATENT DOCUMENTS

| | | | |
|---|---|---|---|
| 5,118,801 | 6/1992 | Lizardi et al. | 536/27 |
| 5,130,238 | 7/1992 | Malek et al. | 435/91 |
| 5,215,899 | 6/1993 | Dattagupta et al. | 435/6 |
| 5,252,723 | 10/1993 | Bhatt | 536/25.3 |
| 5,312,728 | 5/1994 | Lizardi et al. | 435/6 |
| 5,399,491 | 3/1995 | Kacian et al. | 435/91.21 |
| 5,437,990 | 8/1995 | Burg | 435/91.2 |
| 5,474,916 | 12/1995 | Reischl et al. | 436/91.2 |
| 5,514,546 | 5/1996 | Kool | 536/24.3 |
| 5,567,583 | 10/1996 | Wang et al. | 435/6 |
| 5,705,365 | 1/1998 | Ryder et al. | 435/91.1 |
| 5,750,338 | 5/1998 | Collin et al. | 435/6 |
| 5,808,036 | 9/1998 | Kool | 435/6 |
| 5,827,649 | 10/1998 | Rose et al. | 435/6 |

FOREIGN PATENT DOCUMENTS

| | | | |
|---|---|---|---|
| 0329822 | 8/1989 | European Pat. Off. | C12Q 1/68 |
| 0427074 | 5/1991 | European Pat. Off. | C12Q 1/68 |
| 42 13 029 A1 | 4/1992 | Germany | C12P 19/34 |
| 8801302 | 2/1988 | WIPO | C12Q 1/68 |
| 8803957 | 6/1988 | WIPO | C12Q 1/68 |

(List continued on next page.)

OTHER PUBLICATIONS

Adams et al. (editors), "Ch. 2—The Structure of the nucleic acids," *The Biochemistry of the Nucleic Acids*, 11th edition, Chapman & Hall, New York, pp. 5–39 (1992).

Breaker et al., "Continuous in Vitro Evolution of Bacteriophage RNA Polymerase Promoters," *Biochemistry* 33:11980–11986 (1994).

Daubendiek et al., "Rolling–Circle RNA Synthesis: Cricular Oligonucleotides as Efficient Substrates for T7 RNA Polymerase," *J. Am. Chem. Soc.* 117:7818–7819 (1995).

Milligan et al., "Oligoribonucleotide synthesis using T7 TNA polymerase and synthetic DNA templates," *Nucleic Acids Research* 15:8783–8798 (1987).

Nelson, "Detection of Acridinium Esters by Chemiluminescence," in *Nonisotopic DNA Probe Techniques*, edited by Kricka, Academic Press, Inc., San Diego, pp. 275–310 (1992).

Sambrook et al., "Ch. 5—Enzymes Used in Molecular Cloning," in *Molecular Cloning: A Laboratory Manual*, 2nd edition, 1:5.1–5.95 (1989).

*Primary Examiner*—Ardin H. Marschel
*Assistant Examiner*—Joyce Tung
*Attorney, Agent, or Firm*—Christine A. Gritzmacher; Sheldon O. Heber; Carlos A. Fisher

[57] ABSTRACT

The present invention features "promoter-sequestered" oligonucleosides and the use of such oligonucleosides to achieve "target-triggered" amplification. A promoter-sequestered oligonucleoside contains a contiguous nucleic acid sequence which forms a stem-loop structure in the absence of a target sequence. The stem-loop structure contains a single-stranded loop region and a double-stranded stem region. The single-stranded loop contains all, or a portion of, an RNA polymerase promoter sequence. The stem is produced from two substantially complementary nucleic acid sequences able to form an intramolecular hybrid. The secondary structure of the stem decreases the accessibility of the loop promoter sequence to form a functional double-stranded promoter.

37 Claims, 10 Drawing Sheets

FOREIGN PATENT DOCUMENTS

| | | | |
|---|---|---|---|
| 8810315 | 12/1988 | WIPO | C12Q 1/68 |
| 8902439 | 3/1989 | WIPO | C07H 21/02 |
| 89 06700 | 7/1989 | WIPO | C12Q 1/68 |
| 9002820 | 3/1990 | WIPO | C12Q 1/68 |
| 9003446 | 5/1990 | WIPO | C12Q 1/68 |
| 9110746 | 7/1991 | WIPO | C12Q 1/68 |
| 9205287 | 4/1992 | WIPO | C12Q 1/68 |
| 9207864 | 5/1992 | WIPO | C07H 15/12 |
| 9313121 | 7/1993 | WIPO | C07H 21/04 |
| 9322460 | 11/1993 | WIPO | C12Q 1/68 |
| 9322461 | 11/1993 | WIPO | C12Q 1/68 |
| 9402501 | 2/1994 | WIPO | C02H 2/102 |
| 9403472 | 2/1994 | WIPO | C07H 21/04 |
| 9503430 | 2/1994 | WIPO | C12Q 1/68 |
| 9415619 | 7/1994 | WIPO | A61K 3/190 |
| 9419023 | 9/1994 | WIPO | A61K 48/00 |
| 9423069 | 10/1994 | WIPO | C12Q 1/70 |

| SEQ. ID NO. | | Stem/Loop Size |
|---|---|---|
| 1 |  | linear |
| 2 |  | 24/24 |
| 3 |  | 21/15 |
| 4 |  | 26/10 |
| 5 |  | 26/13 |

| SEQ ID NO | | Stem/Loop Sizes |
|---|---|---|
| 13 | ```
          -19              A
    5'-ATTAATACGACTCACT    T
    3'-TAATTATGCTGAGTGA    A
                           G
                          +1
``` | 16/4 |
| 14 | ```
      -19                 +1
                      A T A G
    5'-ATTAATACGACTCACT     GTATAGTCGTGCTATA-3'
``` | Linear |
| 15 | ```
                     -19
                      A
    5'-CTATAGTGAGTCGTAT   T
    3'-GATATCACTCAGCATA   T
                     +1 A
``` | 16/4 |
| 16 | ```
           -19    T T          +1
             A        A
    5'-ATATCGTGCTGATATG    ATACGACTCACTATAG-3'
``` | Linear |
| 17 | ```
                     -19
                      A T  T
    5'-GACCTATAGTGAGTCG       
    3'-CTGGATATCACTCAGC     A
                     +1  A   A
                          T
``` | 16/7 |
| 18 | ```
                   -19 T T
                      A     A
    5'-AAGACCTATAGTGAGT     A
    3'-T TCTGGATATCACTCA    T
                    +1  G  A
                         C
``` | 16/9 |
| 19 | ```
                         A A T A
                     -19 T      C
    5'-CCACCACAAGACCTAT          
    3'-GGTGGTGTTCTGGATA          G
                      +1  T    A
                           C   C
                            A C T
``` | 16/14 |

FIG. 11

PROMOTER-SEQUESTERED OLIGONUCLEOSIDE AND METHOD OF USE

FIELD OF THE INVENTION

The present invention concerns compositions and methods for amplifying nucleic acid using a target nucleic acid sequence to trigger RNA polymerase mediated transcription. The invention is particularly useful as part of a diagnostic procedure to determine whether the target sequence is present in a sample by detecting the production of amplified nucleic acid.

BACKGROUND OF THE INVENTION

RNA polymerase mediated transcription, also referred to herein as "RNA polymerase mediated amplification," is based on the ability of an RNA polymerase to use a nucleic acid template to catalyze ribonucleic acid synthesis. The RNA polymerase synthesizes ribonucleic acid transcripts complementary to the template.

RNA polymerase mediated amplification is initiated by the binding of an RNA polymerase to a promoter region which is usually double-stranded. The RNA polymerase proceeds downstream from the promoter region and synthesizes ribonucleic acid in a 5' to 3' direction. Multiple copies, for example, in the range of 100–3,000, of RNA transcripts are produced by RNA polymerase mediated amplification using a single template.

Factors affecting RNA polymerase mediated amplification efficiency are known to those of ordinary skill in the art. E.g., see, Milligan et al., *Nucleic Acids Research* 15:8783–8798, 1987 ("Milligan et al.") (hereby incorporated by reference herein). Using a linear template most, but not all, of the promoter sequence needs to be part of a double-stranded promoter region for RNA polymerase mediated amplification. For example, Milligan et al. refers to a "bottom strand" which contains the promoter sequence upstream from the template and a "top strand" which is nucleic acid complementary to the bottom strand. Milligan et al. indicates that for T7 RNA polymerase, the top strand can be several nucleotides shorter on either the 3' or 5' terminus of the promoter sequence. According to Milligan et al. at pages 8791–8792:

> As the top strand is shortened from its 3' end, neither the site of initiation nor the amount of products is significantly altered until nucleotide −3 is removed. Further elimination of nucleotides causes a decrease in the amount of full length product, but not any change in the point of initiation, until the nucleotide at −8 is eliminated at which point there are no detectable full length products. A similar, less complete, experiment removing nucleotides from the 5' terminus of the top strand shows no change in the transcription products or yields until nucleotide −14 is removed. Thus, the top strand does not have to cover the entire T7 consensus promoter, but can be up to 3 nucleotides shorter on either the 3' or 5' terminus.

Milligan et al. also indicates that removal of additional top strand bases results in decreasing activity until nucleotide −8 is removed, and removal of nucleotides to −14 resulted in no full length transcription products being observed. Other RNA polymerases, such as T3 RNA polymerase, have similar properties in that a double-stranded promoter is generally needed for transcription activity, however, the promoter sequence need not be completely double-stranded.

Daubendiek et al., *J. Am. Chem. Soc.* 117:7818–7819, 1995 ("Daubendiek et al.") (hereby incorporated by reference herein), indicates that a circular oligonucleotide can serve as a template for T7 polymerase. At page 7818, first column, second paragraph, Daubendiek et al., notes that transcription was said to occur " . . . in the absence of RNA primers, in the absence of RNA promoter sequences, and in the absence of any duplex structure at all."

Transcription templates include RNA and DNA, and may be single-stranded or double-stranded. Kacian et al., U.S. Pat. No. 5,399,491, and Burg et al., U.S. Pat. No. 5,437,990, both illustrate RNA polymerase mediated amplification using a DNA template (both of these references are hereby incorporated by reference herein). Kacian et al., International Publication No. PCT/US93/04015, International Publication No. WO 93/22461, illustrates transcription using an RNA template (hereby incorporated by reference herein).

Transcription, along with other techniques which amplify nucleic acid using a nucleic acid template such as the polymerase chain reaction method (PCR), the ligase chain reaction (LCR), and Qβ replicase are particularly useful as part of a diagnostic technique where amplified nucleic acid is detected to indicate the presence of a target sequence.

Publications mentioning transcription as part of a diagnostic technique include Kacian et al., U.S. Pat. No. 5,399,491; Burg et al., U.S. Pat. No. 5,437,990; Kacian et al., International Publication No. PCT/US93/04015, International Publication No. WO 93/22461; Gingeras et al., International Application No. PCT/US87/01966, International Publication No. WO 88/01302; Gingeras et al., International Application No. PCT/US88/02108, International Publication No. WO 88/10315; Davey and Malek, EPO Application No. 88113948.9, European Publication No. 0 329 822 A2; Malek et al., U.S. Pat. No. 5,130,238; Urdea, International Application No. PCT/US91/00213, International Publication No. WO 91/10746; McDonough et al., International Application No. PCT/US93/07138, International Publication No. WO 94/03472; Kacian et al., International Publication No. PCT/US93/04015, International Publication No. WO 93/22461; and Ryder et al., International Application No. PCT/US94/08307, International Publication Number WO 95/03430.

Different schemes can be employed to bring about transcription in the presence of target sequence. For example, Axelrod et al., International Application No. PCT/US89/03884, International Publication No. WO 90/02820, on page 6, lines 29–35, mentions an "invention":

> . . . predicated on the use of an oligonucleotide probe, suitable for hybridization with a segment of a target nucleic acid sequence, that has linked thereto a moiety that is capable of initiating the production of a plurality of RNA transcripts, themselves containing sequence operable for their multiple self-replication.

Dattagupta, European Patent Application No. 90120652.4, Publication Number 0 427 074 A2, in the abstract asserts:

> Specific nucleic acid sequences are amplified through the use of transcribable hairpin probes. The probe comprises a single stranded self-complementary sequence which, under hybridizing conditions, forms a hairpin structure having a functional promoter region, and further comprises a transcribable sequence extending from the '5 end of the hairpin sequence and a probe sequence which may be comprised in the transcribable 5' sequence or in a sequence extending from the 3' end of the hairpin sequence.

Dattagupta, U.S. Pat. No. 5,215,899, describes the same type of technology as the Dattagupta European patent application.

Lizardi et al., International Application No. PCT/US89/ 04275, International Publication No. WO 90/03446 ("Lizardi et al.,"), describes nucleic acid probes containing "molecular switches." The molecular switches described by Lizardi et al. are closed in the absence of target sequence, but open in the presence of target sequence. According to Lizardi et al. at page 10, lines 13–23:

> This invention involves the use of a nucleic acid hybridization probe comprising at least the following essentials: a probe sequence of approximately 15–115 nucleotides in length surrounded on both sides by complementary nucleic acid sequences which are considerably shorter than the probe sequence, preferably not greatly in excess of one-half the length of the probe sequence. This combination of three sequences forms a simple molecular allosteric switch.

None of the references described herein are admitted to be prior art to the claimed invention.

SUMMARY OF THE INVENTION

The present invention features "promoter-sequestered oligonucleosides" and the use of such oligonucleosides to achieve "target-triggered" amplification. A promoter-sequestered oligonucleoside contains a contiguous nucleic acid sequence which forms a stem-loop structure in the absence of a target sequence. The stem-loop structure contains a single-stranded loop region and a double-stranded stem region. The single-stranded loop contains all, or a portion of, an RNA polymerase promoter sequence. The stem is produced from two substantially complementary nucleic acid sequences able to form an intramolecular hybrid. The secondary structure of the stem decreases the accessibility of the loop promoter sequence to form a functional double-stranded promoter, for example in the presence of an oligonucleotide having a sequence complementary to the promoter sequence.

One of the two stem sequences also contains all, or a portion of, a target-complementary region. In the presence of a target nucleic acid the promoter-sequestered oligonucleoside target-complementary region hybridizes to the target sequence, causing the stem to unfold and thereby increasing the accessibility of the promoter sequence to form a functional double-stranded promoter region, for example in the presence of an oligonucleotide having a sequence complementary to the promoter sequence. RNA polymerase mediated amplification can be carried out after the formation of the functional double-stranded promoter-region.

The promoter-sequestered oligonucleoside is preferably used as part of a diagnostic assay to detect the presence of a target sequence. Such an assay may be carried out by combining the promoter-sequestered oligonucleoside with a sample suspected of having nucleic acid containing the target sequence under conditions and reagents compatible with the formation of a double-stranded promoter region and RNA polymerase mediated amplification, as described in more detail below. The presence of the target sequence triggers amplification. Amplified nucleic acid can be detected to indicate the presence of the target sequence in the sample.

Thus, a first aspect of the present invention features a promoter-sequestered oligonucleoside comprising:

a stem made up of a first and a second nucleic acid sequence which are substantially complementary to each other, and a single-stranded loop region located between the first and second nucleic acid sequences, wherein an RNA polymerase promoter sequence is located substantially within the loop region.

The two substantially complementary sequences making up the stem are located 3' of the loop (i.e., a 3' intramolecular binding region) and 5' of the loop (i.e., a 5' intramolecular binding region). Preferably, the two intramolecular binding regions are perfectly complementary.

The loop region along with the 3' intramolecular binding region and 5' intramolecular binding region are provided as a single nucleic acid strand having nucleoside subunits covalently joined together. Additional oligonucleosides can also be hybridized to the promoter-sequester oligonucleoside. For example, a stem can be formed where a portion of the 3' intramolecular binding region is hybridized to a portion of the 5' intramolecular binding region and also hybridized to a separate oligonucleoside.

The nucleoside subunits making up the promoter-sequestered oligonucleoside can be covalently joined together by different linkages including phosphodiester linkages and phosphorothioate linkages. Preferred sugar moieties for nucleosides are ribose and deoxyribose, and derivatives thereof. More preferably, the sugar moiety is either deoxyribose or 2-methoxyribose.

The target-complementary region is that part of the promoter-sequestered oligonucleoside which hybridizes to the target sequence to form a stable duplex. At least part of the target-complementary region is present in either the 3' intramolecular binding region or the 5' intramolecular binding region. The target-complementary region is sufficiently complementary to the target sequence to form a hybrid therewith under amplifying conditions.

Promoter-sequestered oligonucleoside unfolding is facilitated by using a target-complementary region made up of two parts: (1) a target-complementary subsequence present in the stem; and (2) a target-complementary subsequence which is single-stranded and extends from the stem either 3' of the 3' intramolecular binding region or 5' of the 5' intramolecular binding region. In different embodiments, the stem target-complementary sequence is about 10 to 30 bases in length, about 23 to 28 bases in length, and about 25 bases.

Target-complementary regions extending 3' of the 3' intramolecular binding region or 5' of the 5' intramolecular binding region, are one or more bases in length and substantially complementary to a portion of the target sequence. Preferably the target-complementary sequence extending from the stem is about 10 to 50 bases in length, and more preferably about 15 to 30 bases in length.

The stem can also contain one or more target nonspecific moieties which do not specifically hydrogen bond to a target nucleic acid. Target nonspecific moieties include mismatches, and "universal bases" such as inosine which can hydrogen bond to different bases. Target nonspecific moieties are preferably kept to a minimum. In different embodiments target nonspecific moieties are no more than 20% of the stem, no more than 10of the stem, no more than 5% of the stem, and 0% of the stem.

The presence of non-complementary bases near the loop region may decrease accessibility of the promoter sequence in the presence of target. Preferably, the target-complementary region includes the 3'-end of the 5' intramolecular binding region or the 5'-end of the 3' intramolecular binding region.

The promoter-sequestered oligonucleoside can also contain additional groups 3' of the 3' intramolecular binding region, or 5' of the 5' intramolecular binding region which are not target-complementary nucleosides. Such additional groups should be chosen so they do not prevent the promoter-sequestered oligonucleoside from hybridizing to its target sequence and triggering amplification in the presence of the target sequence. Examples of additional groups include additional nucleosides and amino acids.

Preferably, the promoter-sequestered oligonucleoside comprises a DNA polymerase blocking moiety 5' of the promoter-sequestered oligonucleoside promoter sequence and/or a blocked 3' terminus. A blocking moiety 5' of the promoter-sequestered oligonucleoside promoter sequence is advantageous for preventing formation of a double-stranded promoter region which may occur due to entry of an DNA polymerase 5' of the promoter sequence. A "blocked 3' terminus" refers to the presence of one or more groups at or near the 3' end of the oligonucleoside which inhibits, completely or partially, elongation of the 3' end of the oligonucleoside by a nucleic acid polymerase, such as RNA polymerase. Examples of blocking groups include phosphorothioate, non-nucleotide linkages, alkane-diol residue, and cordycepin. Non-nucleotide linkers and linkages are described by Arnold et al. International Application No. PCT/US88/03173, International Publication No. WO 89/02439, hereby incorporated by reference herein.

Another aspect of the present invention features a method for amplifying a nucleic acid sequence using a promoter-sequestered oligonucleoside, where amplification is triggered by the presence of a target sequence. A functional double-stranded promoter can be formed with the promoter-sequestered oligonucleoside promoter sequence, which is rendered more accessible by hybridization of the promoter-sequestered oligonucleoside to its target, using different techniques. Examples of techniques for forming a functional double-stranded promoter region include hybridization of a promoter-complementary oligonucleotide, primer extension of an oligonucleotide hybridized to the promoter-sequestered oligonucleoside 3' of the promoter sequence, and the use of two or more oligonucleotides which can hybridize to the promoter sequence of the promoter-sequestered oligonucleoside which are then ligated together.

Preferably, a promoter-complementary oligonucleotide having a blocked 3' terminus is used to form a functional double-stranded promoter. Such a promoter-complementary oligonucleotide should be sufficiently complementary to the promoter-sequestered oligonucleoside promoter sequence to form a fully active promoter without having its 3' terminus extended in a polymerase reaction.

Amplification can be carried out under conditions where a first amplification product is used as a target sequence for further amplification. Multiple rounds of amplification can be carried out, where the product of one round of amplification is used as a target sequence for a subsequent round of amplification. Preferably, amplification, and multiple rounds of amplification, are carried out using isothermal transcription mediated amplification conditions.

Another aspect of the present invention features a method for detecting the presence of a target nucleic acid sequence in a sample using a promoter-sequestered oligonucleoside. The method is carried out by combining the promoter-sequestered oligonucleoside with a sample suspected of containing a nucleic acid having a target sequence under amplification conditions and then detecting the presence of a specific amplified sequence as an indication of the presence of target sequence.

Thus, the present invention provides for compositions and methods for triggering amplification in the presence of a target sequence. Expected advantages of using the described promoter-sequestered oligonucleosides in different embodiments and aspects described herein include the following:

the ability to carry out amplification which is facilitated by the presence of a target sequence, and thereby amplified products indicate whether a target sequence is present; the ability to carry out sequence-specific RNA polymerase mediated amplification under isothermal conditions; the ability to carry out RNA polymerase mediated amplification using only one enzyme activity, an RNA polymerase; the ability to trigger amplification using a target sequence present on a target nucleic acid strand with or without a defined end in the absence of a primer which hybridizes to a complementary target strand; and the ability to perform multiple rounds of amplification using the promoter-sequestered oligonucleoside in the absence of a primer which hybridizes to a complementary target strand thereby saving on reagents and eliminating the need to identify two different sequences for primer hybridization. Additionally, it is expected that non-productive amplification side-products may be minimized in such a system.

Various examples are used throughout the application. These examples are not intended in any way to limit the claimed invention.

Other features and advantages of the invention will be apparent from the following figures, detailed description of the invention, examples, and the claims.

BRIEF DESCRIPTION OF THE FIGURES

FIG. 11 provides the nucleic acid sequences, and illustrates the secondary structures, for oligonucleotides of SEQ. ID. Nos. 13–19.

DETAILED DESCRIPTION OF THE INVENTION

Figure 1:
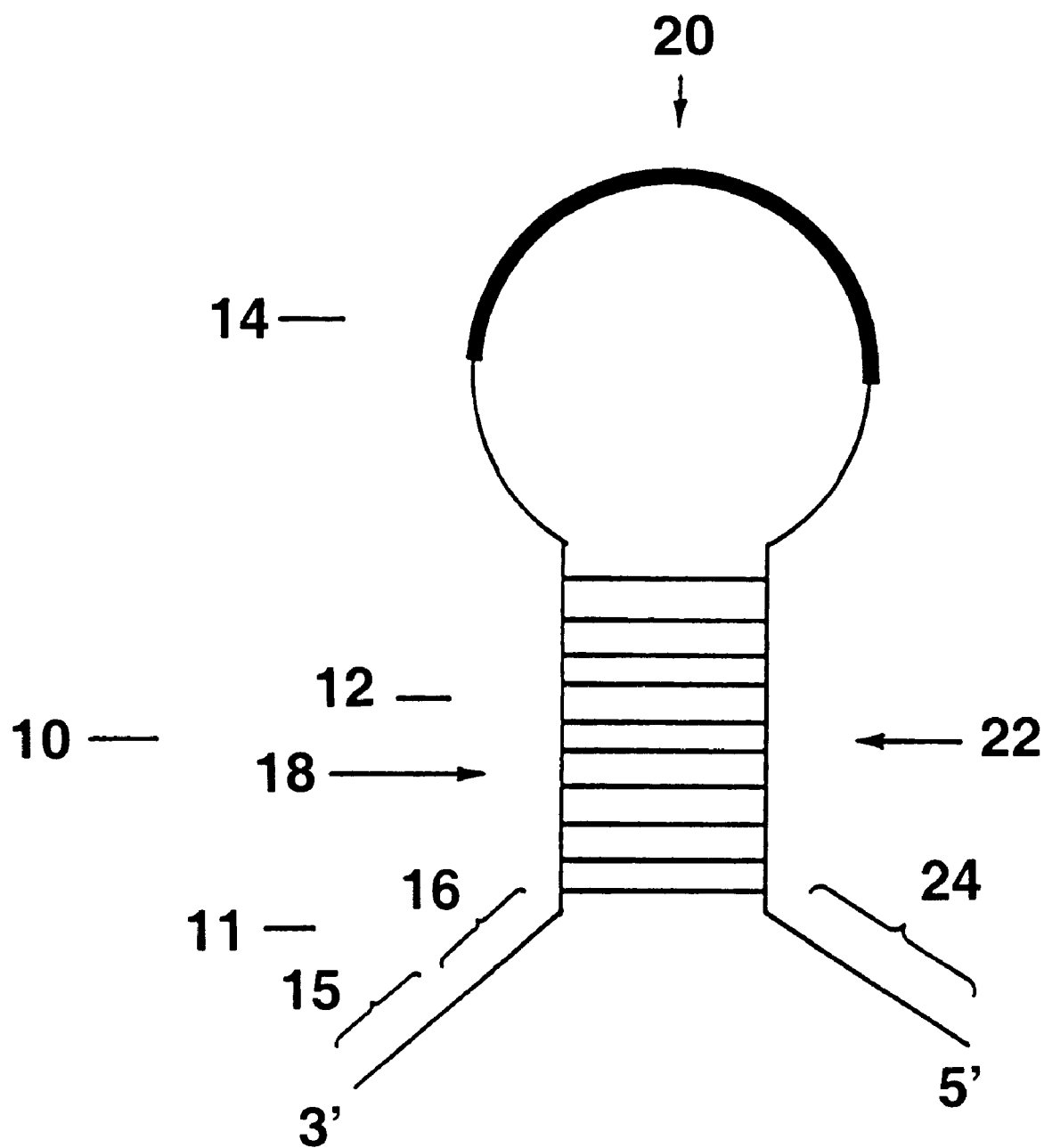
FIG. 1 provides an illustration of a promoter-sequestered oligonucleoside structure.

The present invention features promoter-sequestered oligonucleosides which can be triggered by the presence of a target sequence to amplify a nucleic acid. The promoter-sequestered oligonucleoside can be employed in different schemes to use templates from different sources including nucleic acid present in the target sequence, nucleic acid present in the promoter-sequestered oligonucleoside, and nucleic acid present in an oligonucleotide containing a promoter-complementary sequence and an additional template sequence. FIGS. 1–8 illustrate different promoter-sequestered oligonucleosides, formation of a double-stranded promoter in the presence of a target sequence, and target-triggered amplification in the presence of a target sequence. Various different promoter-sequestered oligonucleoside designs, and amplification schemes involving the promoter-sequestered oligonucleoside are described in these figures and the description provided herein. These different descriptions are not intended to limit the invention, but rather illustrate different aspects and embodiments of the invention.

I. Definitions

Definitions along with preferred embodiments of some of the terms described in the present application are presented in this section. This section is not intended to provide a definition of all of the terms used in the present application, but rather provides a reference section for several of the terms used throughout the application.

"Amplifying conditions" refer to conditions compatible with RNA polymerase mediated amplification by transcription of nucleic acids. Such conditions include the presence of an RNA polymerase, ribonucleotide substrates for the RNA polymerase, appropriate buffer conditions for the RNA polymerase, and an appropriate temperature for the RNA polymerase. The importance of these different conditions is known in the art. E.g., see, Kacian et al., U.S. Pat. No. 5,399,491; Burg et al., U.S. Pat. No. 5,437,990; Gingeras et al., International Application No. PCT/US87/01966, International Publication No. WO 88/01302; Gingeras et al., International Application No. PCT/US88/02108, International Publication No. WO 88/10315; Davey and Malek, EPO Application No. 88113948.9, European Publication No. 0 329 822 A2; Malek et al., U.S. Pat. No. 5,130,238; Urdea, International Application No. PcT/US91/00213, International Publication No. WO 91/10746; McDonough et al., International Application No. PCT/US93/07138, International Publication No. WO 94/03472; Kacian et al., International Publication No. PCT/US93/04015, International Publication No. WO 93/22461; Ryder et al., International Application No. PCT/US94/08307, International Publication Number WO 95/03430; Dattagupta, U.S. Pat. No. 5,215,899; and Dattagupta, European Patent Application 90120652.4, Publication Number 0 427 074 A2. (Each of these references are hereby incorporated by reference herein.)

Amplifying conditions preferably involve incubation at a temperature of about 22° C. to about 42° C., more preferably, incubation is carried out at about 37° C. However, amplification can be carried out at higher or lower temperatures. For example, a higher temperature can be used in conjunction with appropriate promoter-sequestered oligonucleoside constructs having longer length stems and enzymes compatible with the higher temperature. An example of a preferred amplification condition is 16 μL of buffer containing 200 mM tris(hydroxymethyl) aminomethane-HCl (Tris-HCl) (pH 8.1), 50 mM spermidine, 25 mM dithiothrietol (DTT), 250 μg/ml bovine serum albumin (BSA), 0.05% (v/v) Triton® X-100, 400 mg/mL polyethylene glycol (PEG) 8000 and 100 mM $MgCl_2$, 2 μL of 40 mM ATP, GTP, CTP and UTP, 1 μL of RNasin (40 units) and T7 RNA Polymerase (200 units), which are incubated at 37° C. for 2 hours.

Promoter-sequestered "nucleic acid" refers to an oligonucleoside having nucleoside subunits covalently joined together. Preferably, the nucleoside subunits are joined together by phosphodiester bonds to allow for hydrogen-bonding between complementary nucleic acid purine or pyrimidine bases. However, other types of linkages, such as phosphorothioate, methylphosphonate, and non-nucleotide linkages, can be employed to allow for hydrogen-bonding between complementary nucleic acid purine or pyrimidine bases.

"Promoter-complementary oligonucleotide" refers to an oligonucleotide sufficiently complementary to the promoter-sequestered oligonucleoside promoter sequence to hybridize to the promoter sequence under amplifying conditions in the presence of target sequence and form a functional double-stranded promoter region. Preferably, the promoter-complementary oligonucleotide contains a region perfectly complementary to the promoter-sequestered oligonucleoside promoter sequence. The promoter-complementary oligonucleotide can also have a template sequence located 5' of the promoter sequence.

"Functional double-stranded promoter region" refers to a promoter region sufficiently double-stranded such that it is recognized by an RNA polymerase which then can proceed to catalyze RNA polymerase mediated transcription.

"Isothermal" mediated amplification conditions refer to conditions wherein the temperature is not cycled to alternatively: (1) synthesize a complementary nucleic acid duplex; and (2) separate the two complementary strands of the duplex. Preferably, isothermal conditions refer to a constant temperature were little, preferably no, temperature fluctuations occur. Preferably, the temperature stays within a range of ±5° C., more preferably ±2° C., most preferably ±0.5° C.

"Non-complementary region" refers to a nucleic acid sequence which does not hybridize to the target sequence under amplification conditions to trigger amplification. Non-complementary regions located downstream of the promoter sequence can serve as templates for RNA polymerase mediated amplification upon formation of a functional double-stranded promoter region. Amplified non-complementary sequences have different uses, for example, the non-complementary region can be used to produce a reporter sequence which is detected, can be used to produce a sequence which can be immobilized by a capture probe, and can be used to facilitate multiple rounds of amplification by serving as a target sequence after an initial round of amplification.

By "substantially within the loop" is meant all of the promoter sequence, or a sufficient amount of the promoter sequence, is single-stranded so that the promoter sequence contains less than 40% the activity of a double-stranded promoter. In preferred embodiments the promoter sequence contains less that 20%, less than 10%, and less than 5% of the activity of a fully double-stranded promoter.

By "substantially complementary" is meant two nucleic acid strands having a sufficient amount of complementarity to form a stable nucleic acid duplex under amplifying conditions. Preferably, substantially complementary sequences are perfectly complementary.

"Target sequence" refers to a nucleic sequence which can hybridize to a region of the promoter-sequestered oligonucleoside under amplifying conditions. Preferably, the target sequence is a nucleic acid sequence sought to be detected. More preferably, the target sequence is a naturally occurring sequence, even more preferably, the target sequence is a sequence present in a cell, tissue or organism. Examples of preferred target sequences include sequences characteristic of a human gene, microorganism, group of microorganisms, or a virus.

Target-complementary regions able to hybridize to the target sequence can be designed using standard techniques taking into account the use of the promotor-sequestered oligonucleoside. For example, promoter-sequestered oligonucleosides used in diagnostic assays are preferably designed to specifically hybridize to the target sequence in the presence of related non-target sequences. Numerous references have been published describing the design of oligonucleosides to specifically hybridize to a target sequence. For example, Hogan et al., International Application No. PCT/US88/03009, International Publication Number Wo 88/03957 describes the design of oligonucleoside probes able to detect the presence of a microorganism or group of microorganisms; McDonough et al., International Application No. PCT/US94/03130, Publication No. WO 94/23069 and McDonough et al., International Application No. PCT/US93/04004, Publication No. WO 93/22469, describe oligonucleoside probes to detect the presence of a virus by hybridization to a sequence characteristic of the virus; and Sambrook et al., *Molecular Cloning: A Laboratory Manual* (Cold Spring Harbor Laboratory Press, 1989) describes different factors affecting oligonucleotide specificity such as the degree of complementarity between the oligonucleotide and target nucleic acid sequences and the hybridization conditions. (Each of these references are hereby incorporated by reference herein.)

II. Promoter-Sequestered Oliconucleoside Design

Promoter-sequestered oligonucleosides have a stem-loop structure where the loop region contains all or part of a promoter sequence. The stem contains two substantially complementary nucleic acid sequences able to form a hybrid under amplifying conditions. One of the two sequences making up the stem also contains a target-complementary region which is substantially complementary to a region of the target nucleic acid. A single-stranded promoter sequence is located substantially within the loop. Numerous variations of the promoter-sequestered oligonucleoside can be constructed based on the teachings provided herein.

An example of a promoter-sequestered oligonucleoside is provided in FIG. 1. Referring to FIG. 1, a promoter-sequestered oligonucleoside (10) is shown having a stem-loop secondary structure. The stem (12) is held together by intramolecular hydrogen bonding between two substantially complementary sequences: a 3' intramolecular binding region (18) and a 5' intramolecular binding region (22). The loop (14) is single-stranded. The stem (12) is covalently joined at its 3' end to a single-stranded nucleic acid region (11), and covalently joined at its 5' end to another single-stranded nucleic acid region (24). The 3' end region (11) contains a non-complementary region (15) joined to the 3' end of the single-stranded nucleic acid region (16).

The target-complementary region shown in FIG. 1 is located 3' of the loop region and is made up of the 3' intramolecular binding region (18) and the single-stranded nucleic acid region (16). The 5' end of the intramolecular binding region (18) is covalently joined to the 3' end of the loop region (14) which is shown containing a single-stranded promoter sequence (20) (shown by a thick line). The 5' end of the loop region (14) is covalently joined to the 3' end of the 5' intramolecular binding region (22), which is covalently joined at its 5' end to the 3' end of a 5' nucleic acid sequence (24).

Single-stranded regions such as 11 and 24 shown in FIG. 1 are potential sites for RNA polymerase invasion in the absence of a target sequence. Thus, it is desirable to have one or more RNA polymerase inhibitory sites on the promoter-sequestered oligonucleoside which decrease, and preferably, prevent RNA polymerase invasion in the absence of target nucleic acid. Examples of RNA polymerase inhibitory sites include non-nucleotide linkers placed in a single-stranded region or the stem. RNA polymerase inhibitory sites should not be positioned on nucleic acid which is intended to be used as a template.

Figures 2A, 2B, 2C:
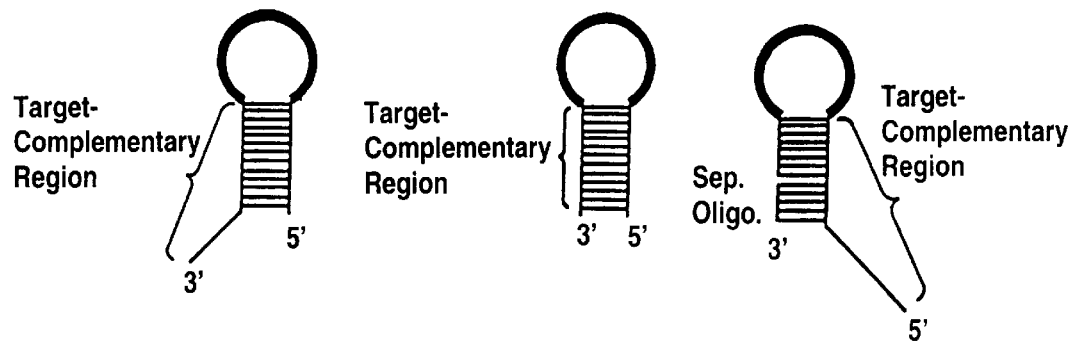
FIGS. 2A, 2B, and 2C provide illustrations of different promoter-sequestered oligonucleoside configurations. A promoter sequence is shown by a thick line.

FIG. 2 provides examples of promoter-sequestered oligonucleosides having different placements of target-complementary regions. Referring to FIG. 2, FIG. 2A shows a target-complementary region which extends the 3' end of the promoter-sequestered oligonucleoside; FIG. 2B shows a promoter-sequestered oligonucleoside in which the target-complementary region is contained wholly within the intramolecular binding region; and FIG. 2C shows a target-complementary region which extends into a single-stranded region 5' of the 5' intramolecular binding region. FIG. 2C, also illustrates a promoter-sequestered oligonucleoside containing a separate additional oligonucleoside, shown as "Sep. Oligo."

Figures 3A, 3B, 3C:
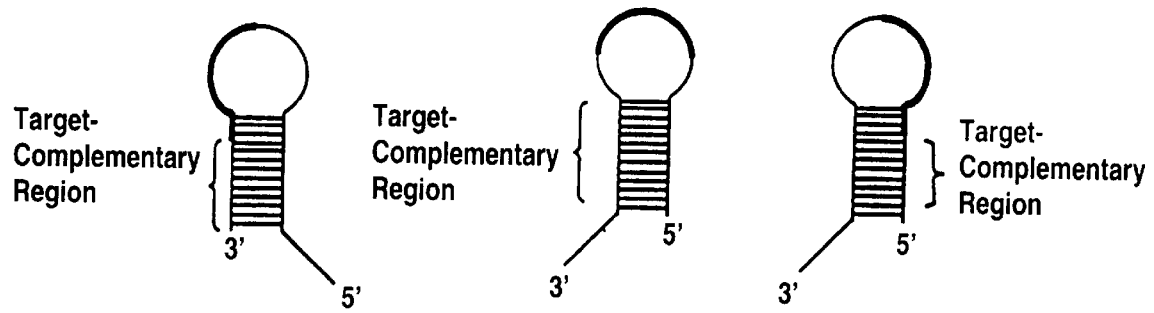
FIGS. 3A, 3B, and 3C provide examples of sequestered promoter sequence locations and target-complementary region locations.

FIG. 3 provides examples of promoter sequence locations in the loop region and provides examples of different placements for target-complementary regions. Referring to FIG. 3, FIG. 3A illustrates a target-complementary region present in part of the 3' intramolecular binding region and a promoter sequence which extends into part of the 3' intramolecular binding region; FIG. 3B illustrates a target-complementary region present in the 3' intramolecular binding region and a promoter sequence which is exclusively present in the loop; and FIG. 3C illustrates a target-complementary region present in part of the 5' intramolecular binding region and a promoter sequence which extends into part of the 5' intramolecular binding region. In a preferred embodiment, the promoter sequence is positioned so that transcription starts 0–4 bases from the 3' end of the 5' intramolecular binding region.

In different embodiments describing the loop region in relation to the size of the promoter sequence, the loop region is no more than twice the size of the promoter sequence, no more than one and a half times the size of the promoter sequence, or about 4 bases greater in size than the promoter sequence.

Different promoter sequences able to form a functional double-stranded promoter region can be incorporated into a promoter-sequestered oligonucleoside. Examples of suitable promoter sequences include those recognized by T7, T3, or SP6 RNA polymerases. In general, preferred RNA polymerases are those that recognize and utilize a double-stranded promoter region, exhibit specificity for a promoter sequence, transcribe RNA at a suitable rate, and make a sufficient number of copies of RNA to achieve the desired level of amplification. Preferably, the promoter-sequestered oligonucleoside contains a promoter sequence not found in the sample being tested when the promoter-sequestered oligonucleoside is used for diagnostic purposes.

RNA polymerase mediated amplification involves adding nucleotide substrates to a growing nucleotide polymer in a 5' to 3' direction using a nucleic acid template strand running 3' to 5'. When a functional double-stranded promoter region is present in a nucleic acid duplex, RNA polymerase mediated amplification can occur using one of the two duplex strands as a template depending upon the orientation of the promoter.

Figure 4:
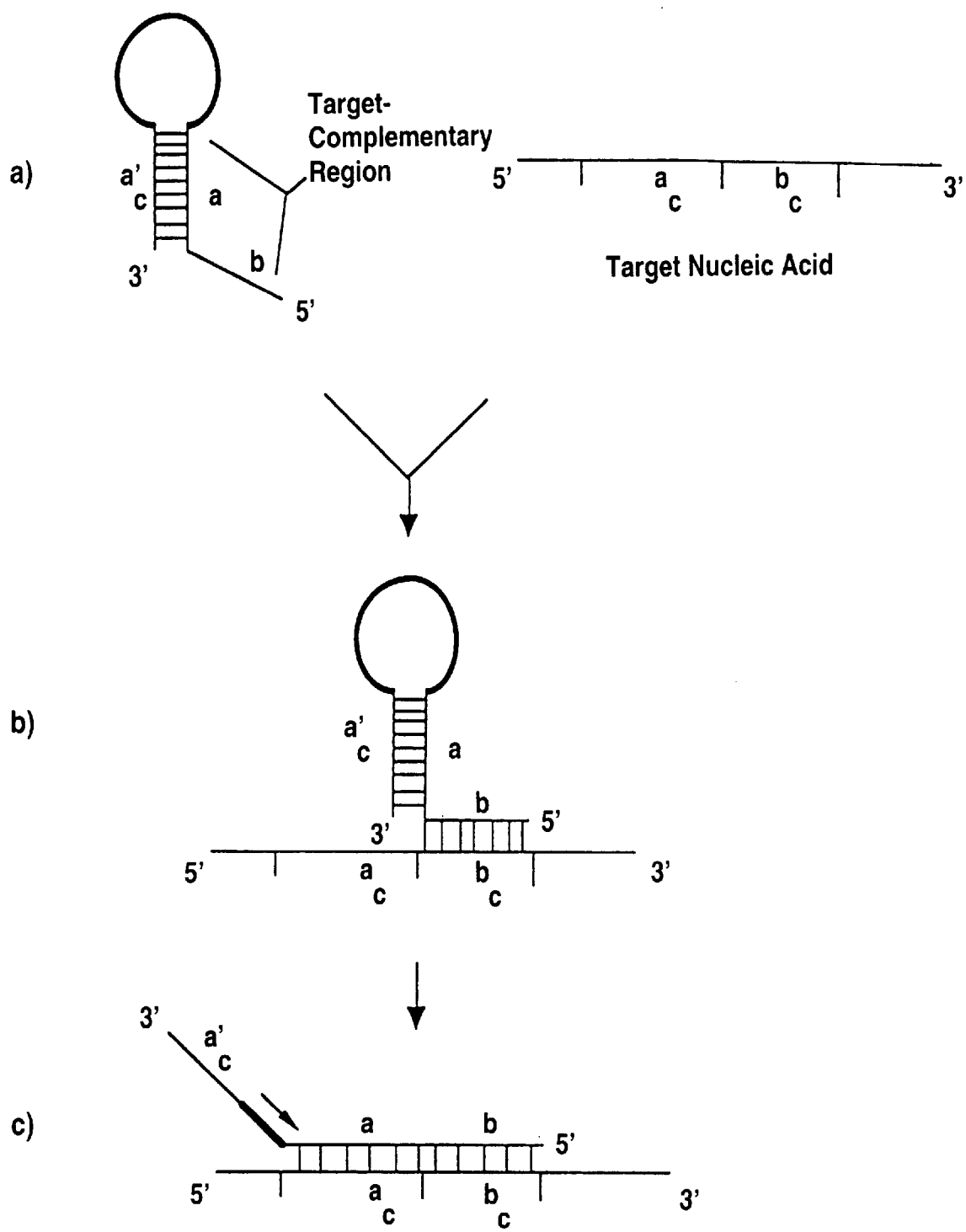
FIG. 4 provides an illustration of promoter-sequestered oligonucleoside unfolding upon hybridization to a target nucleic acid sequence. The promoter-sequestered oligonucleoside promoter sequence is shown by a thick line. The arrow above the promoter sequence indicates the direction of RNA polymerase-mediated transcription.

FIG. 4 illustrates one way in which a promoter-sequestered oligonucleoside having a 5' target-complementary region, where part of the target-complementary region consists of a single-stranded region 5' to the 5' intramolecular binding region, hybridizes to target sequence and, thereby, renders the promoter sequence more accessible for double-stranded promoter formation. Referring to FIG. 4, in step (a) the promoter-sequestered oligonucleoside is combined with nucleic acid containing a target nucleic acid sequence. The promoter-sequestered oligonucleoside is shown having a target-complementary region having two subsequences. The subsequence a is located in the 5' intramolecular binding region. The subsequence (b) extends from the 5' end of the 5' intramolecular binding region and is contiguous with subsequence a. A 3' intramolecular binding region complementary to a is present $a'_c$. A sequestered promoter region is shown by a thick line within the loop. The target region is shown having two parts: $a_c$ which is complementary to a, and ($b_c$) which is complementary to (b). Step (b) illustrates hybridization of subsequence (b) to complementary target region ($b_c$). Step (c) illustrates hybridization of subsequence a to complementary target region $a_c$ and unfolding of the stem-loop.

Stem-loop unfolding is thermodynamically favored because the promoter-sequestered oligonucleoside target-complementary sequence a–b is longer than the shorter length intrastrand complement $a'_c$–a. The longer length interstrand oligonucleoside:target hybrid has a higher $T_m$ and is more stable than the shorter length intrastrand oligonucleoside hybrid.

The relative strengths of the interstrand and intrastrand hybrids should be such that the promoter is effectively sequestered in the absence of target, but effectively accessible when target is present. The relative strengths of the hybrids can be adjusted, for example, by varying the relative lengths of the sequences, choosing regions such that differences in base composition afford increased discrimination, and/or incorporating modified bases into the intramolecular binding region (preferably into the non-target-complementary region) that alter duplex stability. Methods of altering the stabilities of nucleic acid duplexes are well-known to those of ordinary skill in the art. See, for example, *The Biochemistry of the Nucleic Acids* (11th ed. Adams, ed. 1992), Chapter 2.

The target-complementary region should be designed to be sufficiently complementary to a target nucleic acid to hybridize under amplification conditions. Amplification is carried out using stringency conditions compatible with RNA polymerase activity. Under such conditions, the likelihood of hybridization to non-target sequences increases compared to high stringency conditions such as those typically used to detect a target sequence with a detection probe.

Under low stringency hybridization conditions the degree of non-complementarity between two nucleic acid strands that is compatible with the formation of stable hybrids increases. Unfolding of the promoter-sequestered oligonucleoside stem involves breaking apart intramolecular hydrogen bonds within the stem and forming an intermolecular hybrid with the target sequence. Thus, promoter-sequestered oligonucleosides should be designed were the two nucleic acid sequences making up the stem are highly complementary, preferably perfectly complementary. Such promoter-sequestered oligonucleosides will require a high degree of complementarity between the target-complementary region and the target sequence to achieve stem unfolding. Preferably, the target-complementary nucleic acid sequence has at least 8 out of 10 contiguous nucleosides perfectly complementary to a target sequence, more preferably at least 9 out of 10 bases, and even more preferably at least 10 out of 10 perfectly complementary bases.

The promoter-sequestered oligonucleoside can be used in a diagnostic assay, or for other applications where target sequences may be present. In diagnostic applications, the stability of hybrids formed between the target-complementary region and non-target sequences should also be considered. Design of promoter-sequestered oligonucleosides for such applications is preferably done by identifying target regions suitable for specific hybridization with oligonucleotide probes under RNA polymerase mediated amplification conditions. The choice of a particular RNA polymerase will dictate the RNA polymerase mediated amplification conditions. If an appropriate target sequence for a promoter-sequestered oligonucleoside cannot be identified for use with a particular RNA polymerase under a particular set of amplification conditions, hybridization stringency may be altered by adjusting reaction conditions such as by using a different polymerase with different requirements for divalent cation concentration, total ionic strength, and pH.

Once candidate target and target-complementary sequences have been identified, the size and composition of the different parts of the target-complementary subsequences within and outside of the intramolecular binding region can be adjusted to achieve sufficient discrimination between the stabilities of the interstrand target:promoter-sequestered oligonucleoside hybrid and the intrastrand promoter-sequestered oligonucleoside hybrid.

Preferably, promoter-sequestered oligonucleosides having DNA target-complementary regions are used in conjunction with RNA targets to facilitate unfolding of the promoter-sequestered oligonucleoside. RNA:DNA hybrids have a higher $T_m$ and hybridization rate compared to DNA:DNA hybrids having the same base sequence. Thus, the RNA:DNA interstrand hybrid formed between the promoter-sequestered oligonucleoside and RNA target is more stable than the promoter-sequestered oligonucleoside intrastrand DNA:DNA hybrid allowing the RNA target to out compete the intrastrand promoter-sequestered oligonucleoside for the target-complementary region.

III. Promoter-Sequestered Oligonucleoside Construction

Promoter-sequestered oligonucleosides having a particular nucleic acid base composition can be constructed using standard techniques. The promoter-sequestered oligonucleoside may be comprised solely of the common individual nucleoside monophosphates, adenosine, thymidine, guanosine, and cytosine. The promoter-sequestered oligonucleoside may also contain different combinations of one or more, ribonucleosides, modified ribonucleosides, deoxyribonucleosides, and modified deoxyribonucleosides, joined by phosphodiester linkages or non-phosphodiester linkages.

Different deoxynucleosides, deoxyribonucleosides and modifications thereof, and internucleoside linkages, can be used as long as the modification and linkage allows the promoter-sequestered oligonucleoside to trigger amplification in the presence of target sequence. Modifications and linkages which should be avoided include those which destabilize the promoter-sequestered oligonucleoside such that a stem-loop is not formed in the absence of target under amplifying conditions, those which do not allow the promoter-sequestered oligonucleoside to form hydrogen bonds with complementary nucleotides present on the target sequence and which would thereby prevent hybridization to the target sequence, those which inhibit or prevent RNA polymerase binding to the desired template, and those which abolish RNA polymerase activity using the desired template.

Different types of nucleosides can affect promoter activity. For example, ribonucleosides present in the promoter sequence decrease RNA polymerase activity.

Certain modifications to nucleosides or linkages joining nucleosides can influence the $T_m$ of the intrastrand promoter-sequestered oligonucleoside duplex, can influence the $T_m$ of the promoter-sequestered oligonucleoside:target duplex, and can influence promoter activity.

Examples of nucleoside modifications include modified purine or pyrimidine bases such as $N^4$-methyl deoxygaunosine, deaza or aza purines and pyrimidines used in place of natural purine and pyrimidine bases, pyrimidine bases having substituent groups at the 5 or 6 position, and purine bases having an altered or a replacement substituent at the 2, 6 or 8 positions. See, Cook International Application No. PCT/US92/11339, International Publication No. WO 93/13121 (hereby incorporated by reference herein).

Another example of nucleoside modifications are those to the sugar moieties such as the presence of a 2'-alkoxy (see, Miller et al., International Application No. PCT/US94/00157, International Publication No. WO 94/15619; and McGee et al., International Application No. PCT/US93/06807, International Publication Number WO 94/02051, both of which are hereby incorporated by reference herein); "gapped" 2' modified oligonucleosides (see, Cook International Application No. PCT/US92/11339, International Publication No. WO 93/13121); and cyclobutyl moieties connected by linking moieties, where the cyclobutyl moieties have heterocyclic bases attached thereto as described by Cook et al., International Application No. PCT/US93/01579, International Publication No. WO 94/19023 (hereby incorporated by reference herein).

Examples of different linkages which can be used to join nucleosides of a promoter-sequestered oligonucleoside include phosphodiester linkages, phosphorothioate linkages, methylphosphonate linkages, and non-nucleotide linkages.

Organic synthesis of oligonucleosides can be carried out by joining nucleosides in a step wise fashion. Publications describing organic synthesis of oligonucleosides include Eckstein, F., Oligonucleotides and Analogues, *A Practical Approach*, chapters 1–5, 1991, which reviews organic synthesis of oligonucleotides; Caruthers et al., In *Methods In Enzymology* vol. 154 p. 287 (1987), which describes a procedure for organic synthesis of oligonucleosides containing phosphodiester linkages using standard phosphoramidite solid-phase chemistry; Bhatt, U.S. Pat. No. 5,252,723, which describes a procedure for organic synthesis of oligonucleosides containing phosphorothioate linkages; and Klem et al., WO 92/07864, which describes organic synthesis of oligonucleosides having different internucleoside linkages including methylphosphonate linkages. (Each of these references are hereby incorporated by reference herein.)

Different modifications can be made at or near the 3' end of a promoter-sequestered oligonucleoside to obtain a blocked 3' terminus. Modifications to nucleic acid to inhibit elongation of a 3' nucleic acid terminus by a nucleic acid polymerase, completely or partially, are described by Kacain et al., International Application Number PCT/US93/04015, International Publication Number WO 93/22461, hereby incorporated by reference herein. Suitable blocking groups such as 3' terminal phosphorothioate, 3'-non-nucleotide linkage, 3' alkane-diol residue, and 3'-cordycepin, can be incorporated into an oligonucleoside using standard techniques. For example, phosphorothioate linkages can be obtained using techniques referenced above, non-nucleotide linkage synthesis can be carried out as described by Arnold et al. International Application No. PCT/US88/03173, International Publication No. WO 89/02439, and alkane-diol modification can be carried out as described by Wilks et al. *Nucleic Acids Res.* 18:2065, 1990.

IV. Amplification of Nucleic Acid Sequences

Amplification of nucleic acid sequences can be carried out using one or more promoter-sequestered oligonucleosides. Depending upon the design of the promoter-sequestered oligonucleoside and the amplification scheme employed, nucleic acid sequences present on the promoter-sequestered oligonucleoside or nucleic acid not present on the promoter-sequestered oligonucleoside can be amplified. For example, the promoter-sequestered oligonucleoside can be designed to amplify target nucleic acid present on a target strand, nucleic acid present on a promoter-sequestered oligonucleoside, and nucleic acid complementary to that present on a promoter-sequestered oligonucleoside. Additionally, non-complementary sequences added to the 5' end of the promoter-sequestered oligonucleoside and sequences present on target nucleic acid located 5' to the target sequence can also be amplified.

A double-stranded promoter region for RNA polymerase mediated amplification according to the present method can be produced using different techniques including the following: (1) hybridization of a promoter-complementary oligonucleotide to the promoter-sequestered oligonucleoside promoter sequence; (2) hybridization of an extendable primer 3' of the promoter-sequestered oligonucleoside promoter sequence followed by primer extension; and (3) by using nicking or cutting agents, such as restriction endonucleases, to produce a free 3'—OH terminus on one strand followed by primer extension from that 3' terminus.

Figure 5:
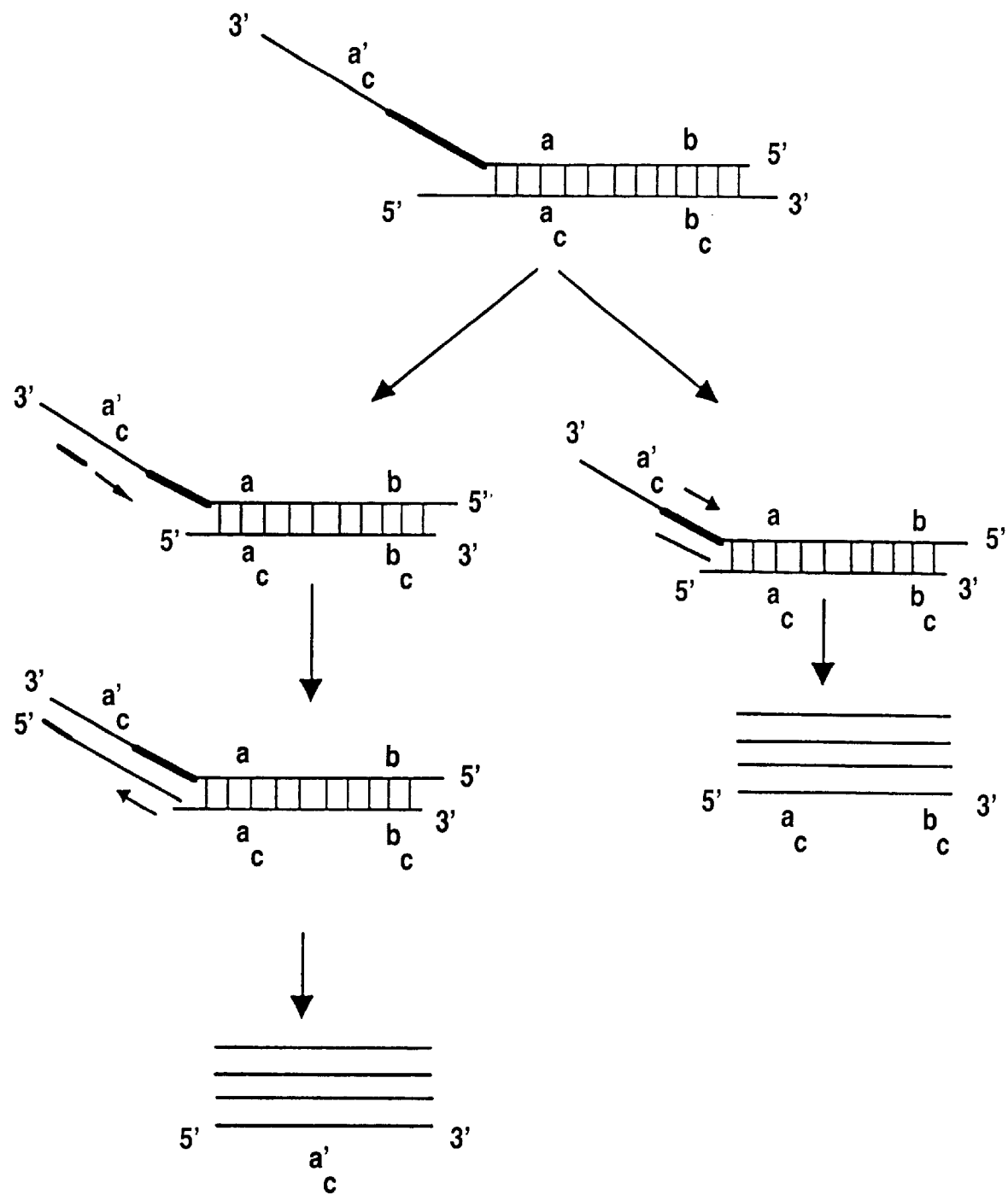
FIG. 5 provides an illustration of how a double-stranded promoter region may be formed using a promoter-sequestered oligonucleoside having a target-complementary region 5' of the loop region, and the production of RNA transcripts from promoters of different orientations. The generation of a double-stranded promoter region by hybridization of a promoter-complementary oligonucleotide is illustrated by the left side of the figure. The generation of a double-stranded promoter region by extension of a primer hybridized 3' of the promoter sequence is illustrated by the right side of the figure. The promoter-sequestered oligonucleoside promoter sequence is shown as a thick line. The arrow above or below the promoter sequence indicates the direction of RNA polymerase mediated transcription.
Figure 6:
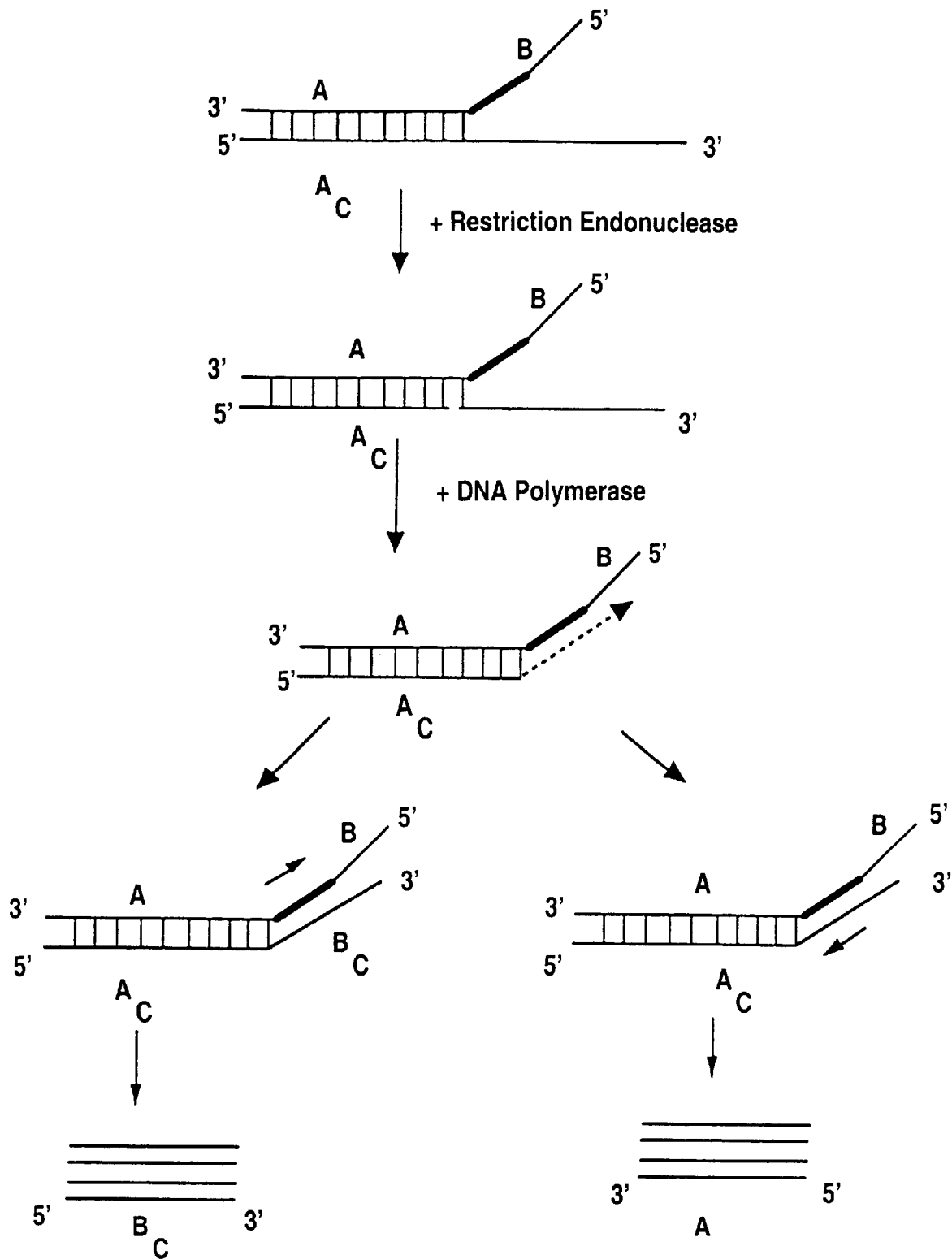
FIG. 6 illustrates the formation of a double-stranded promoter region, after hybridization of a promoter-sequestered oligonucleoside with a target sequence, and the production of RNA transcripts from promoters of different orientation. The double-stranded promoter region is generated using a cutting agent, such as a restriction endonuclease, to generate a free 3'—OH terminus within the region hybridized to the target, and a DNA polymerase to extend that 3' terminus. The promoter-sequestered oligonucleoside promoter sequence is shown as a thick line. The arrow above or below the promoter sequence indicates the direction of RNA polymerase mediated transcription.

FIGS. 5 and 6 illustrate different techniques which can be used to form a double-stranded promoter region. Referring to FIG. 5, the left hand side illustrates the formation of a double-stranded promoter using a primer which hybridizes 3' to the promoter and which is extended using a DNA polymerase. Examples of DNA polymerases suitable for this purpose include DNA polymerase from *Thermus aquaticus* (Taq DNA polymerase) and T4 DNA polymerase. Suitable reaction conditions for these and other suitable DNA polymerase are known to those of ordinary skill in the art. (E.g., See, Sambrook, et al., Molecular Cloning: A Laboratory Manual (2d. ed. 1989), Volume 1, Chapter 5.)

According to this strategy, the primer can be designed to hybridize at various distances from the promoter and may even hybridize to a portion of the promoter. The primer may also be complementary to a portion of the target sequence. Primers having any complementarity to a portion of the target sequence should be designed so as not to cause stem-loop unfolding in the absence of the target sequence. The primer should be complementary to only a small portion of the target sequence, if at all.

The left hand side of FIG. 5 also illustrates the use of a promoter sequence oriented to use the sequence present on the strand complementary to the promoter-sequestered oligonucleoside as a template. If a promoter sequence of the opposite orientation was used in the left hand side of FIG. 5, multiple copies of $a_c$–$b_c$, rather than $a'_c$, would have been produced.

The right hand side of FIG. 5, illustrates the use of a promoter-complementary oligonucleoside to form a double-stranded promoter region by hybridizing to the promoter sequence. The production of multiple copies of nucleic acid complementary to a promoter-sequestered oligonucleoside sequence 5' to the promoter region is shown in the figure.

FIG. 6 illustrates the formation of a double-stranded promoter using a nicking or cutting agent and a nucleic acid polymerase, and amplification using promoters of different orientations. Different cutting agents may be used to selectively nick or cut the target nucleic acid within the promoter-sequestered oligonucleoside:target duplex. Examples of suitable cutting agents/promoter-sequestered oligonucleoside combinations include: (1) restriction endonucleases, in conjunction with a promoter-sequestered oligonucleoside containing a site providing resistance to endonuclease cutting so that only the target nucleic acid strand is cut by the restriction endonuclease; and (2) enzymes having RNase H activity, in conjunction with a promoter-sequestered oligonucleoside having deoxynucleotides located 3' of the promoter and present in a promoter-sequestered oligonucleoside:RNA target duplex. Examples of nuclease-resistant cleavage sites compatible with different restriction endonucleases are provided by Richards, Publication No. WO 92/05287, hereby incorporated by reference herein.

Preferred restriction enzymes for use as nicking or cutting agents are those which are active under amplification conditions. Two factors in choosing appropriate restriction enzymes are the conditions in which they are active and the relative speed of the restriction enzyme cleavage reaction as compared to RNA polymerase activity. For example, if the restriction enzyme is active under RNA polymerase mediated amplification conditions, little amplification may occur due to one strand of the promoter region being continuously cut off. However, signification amplification can be achieved by balancing conditions compatible with both transcription mediated amplification and restriction enzyme activity.

Alternatively, RNA polymerase mediated amplification conditions can be employed which are incompatible with restriction enzyme activity. In this instance, after cutting with a restriction enzyme, the conditions can be adjusted to facilitate amplification and inhibit restriction enzyme activity.

Enzymes having RNase H activity for use in this embodiment should be chosen to be compatible with the promoter-sequestered oligonucleoside sequence. For example, RNase H found in avian myeloblastosis virus (AMV) reverse transcriptase and Moloney murine leukemia virus (MMLV) reverse transcriptase cut RNA of an RNA:DNA duplex at particular sites. (See, e.g., Kacian et al., U.S. Pat. No. 5,399,491 hereby incorporated by reference herein). RNase H enzymes having such cleavage specificity are preferred since the use of such enzymes will leave a sufficient portion of target RNA intact to prime the synthesis of a double-stranded promoter region.

However, RNase H enzymes having less specificity can also be used by adjusting the promoter-sequestered probe composition accordingly. The nucleoside composition of a promoter-sequestered oligonucleoside can be adjusted to contain sites which provide RNA present in an RNA:promoter-sequestered oligonucleoside hybrid with resistance to RNase H activity. For example, the promoter-sequestered oligonucleoside target complementary region can contain nucleosides unable to serve as substrates for RNase H such as ribonucleosides which when present in an RNA:RNA duplex would prevent the target RNA from being cut by RNase H activity.

Figure 7:
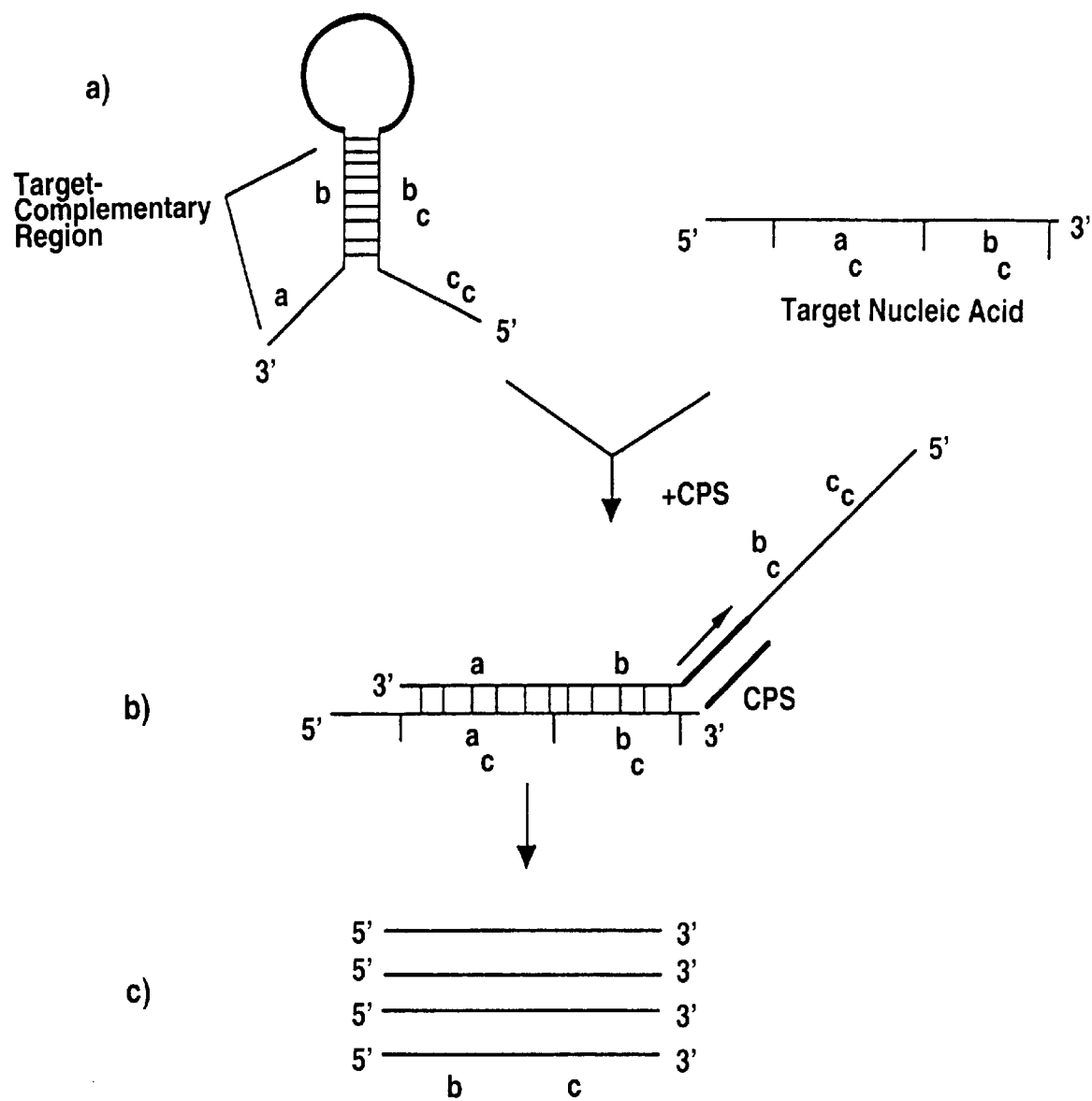
FIG. 7 illustrates target-triggered amplification using a promoter-sequestered oligonucleoside having a target-complementary region extending 3' of the stem and a promoter sequence oriented so that the 5' region of the oligonucleoside is used as a template for RNA transcription. The promoter-sequestered oligonucleoside promoter sequence is shown as a thick line. The arrow above the promoter sequence indicates the direction of RNA polymerase mediated transcription. "CPS" refers to a promoter-complementary oligonucleotide having a complementary promoter sequence.
Figure 8:
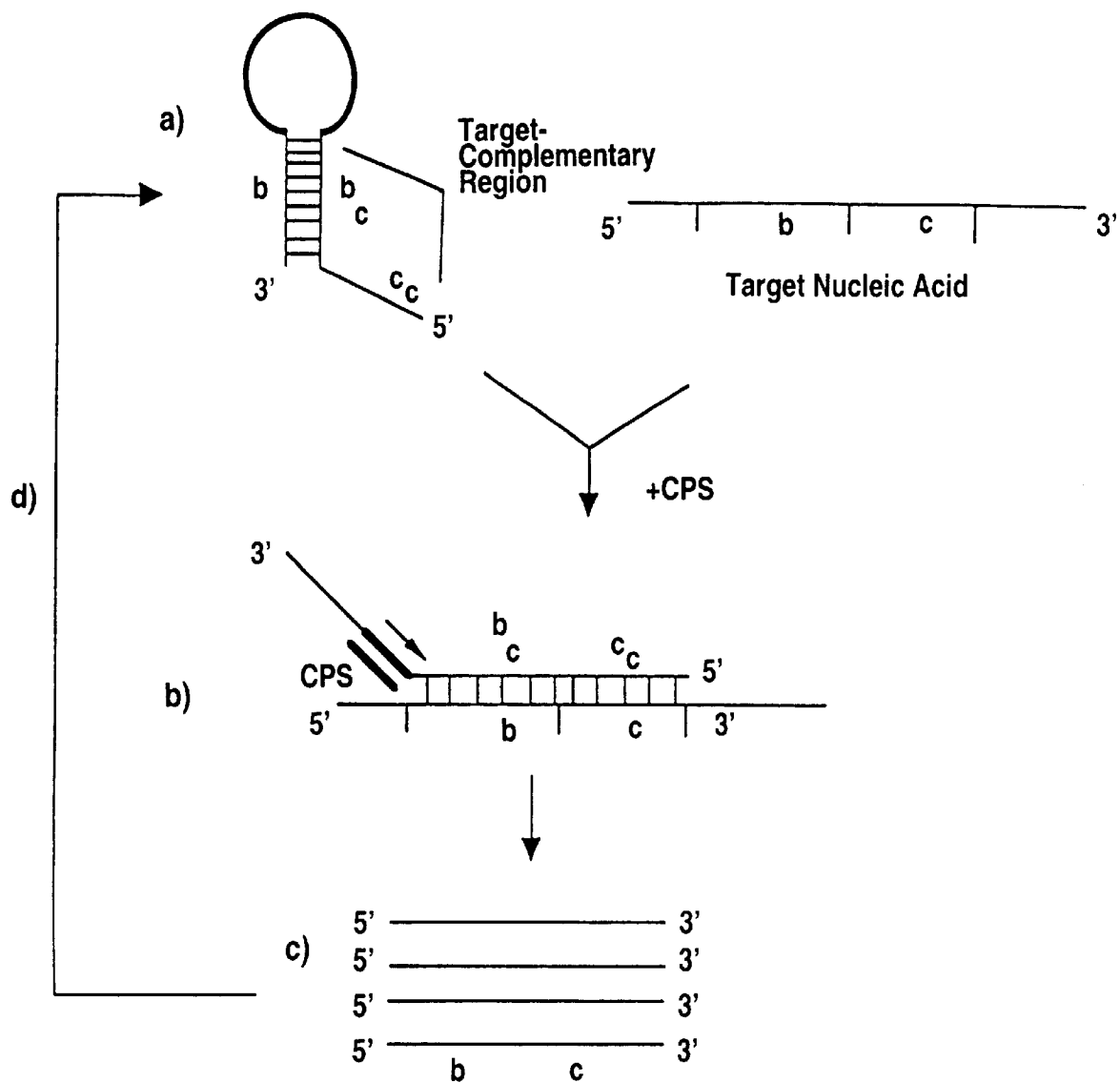
FIG. 8 illustrates multiple rounds of target-triggered amplification using a promoter-sequestered oligonucleoside having a target-complementary region extending 5' of the stem. The promoter-sequestered oligonucleoside promoter sequence is shown as a thick line. The arrow above the promoter sequence indicates the direction of RNA polymerase mediated transcription.
Figure 9:
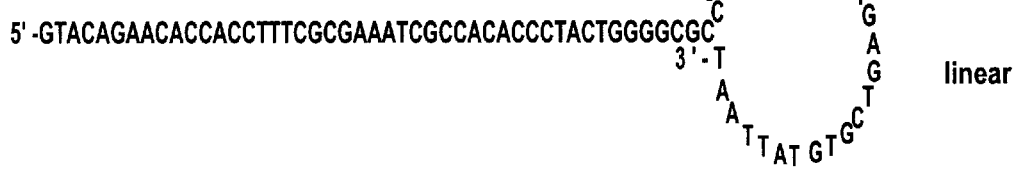
FIG. 9 provides the nucleic acid sequences, and illustrates the secondary structures, for oligonucleotides of SEQ. ID. Nos. 1–5. The arrow indicates the start site and the direction of transcription.
Figure 9:
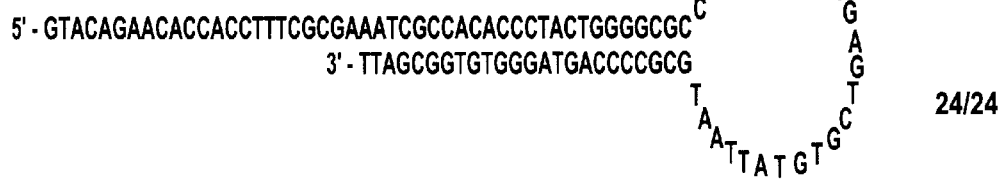
Figure 9:
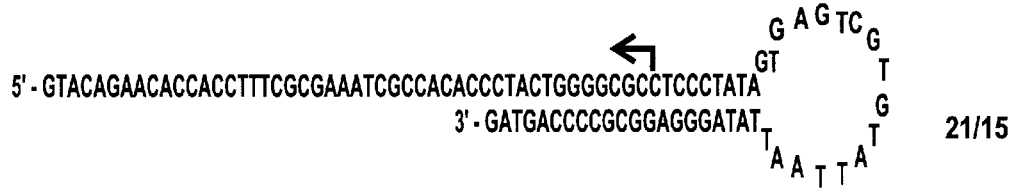
Figure 9:
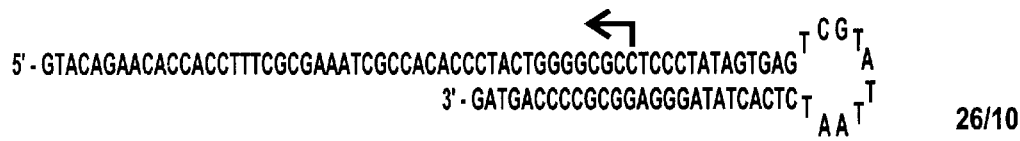
Figure 9:
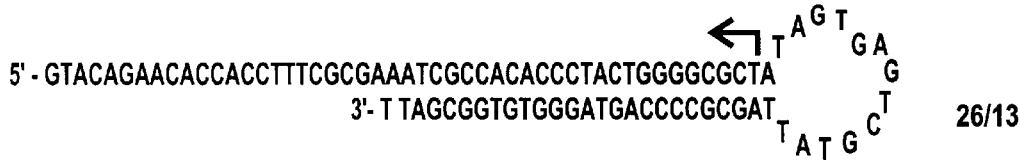
Figure 10:
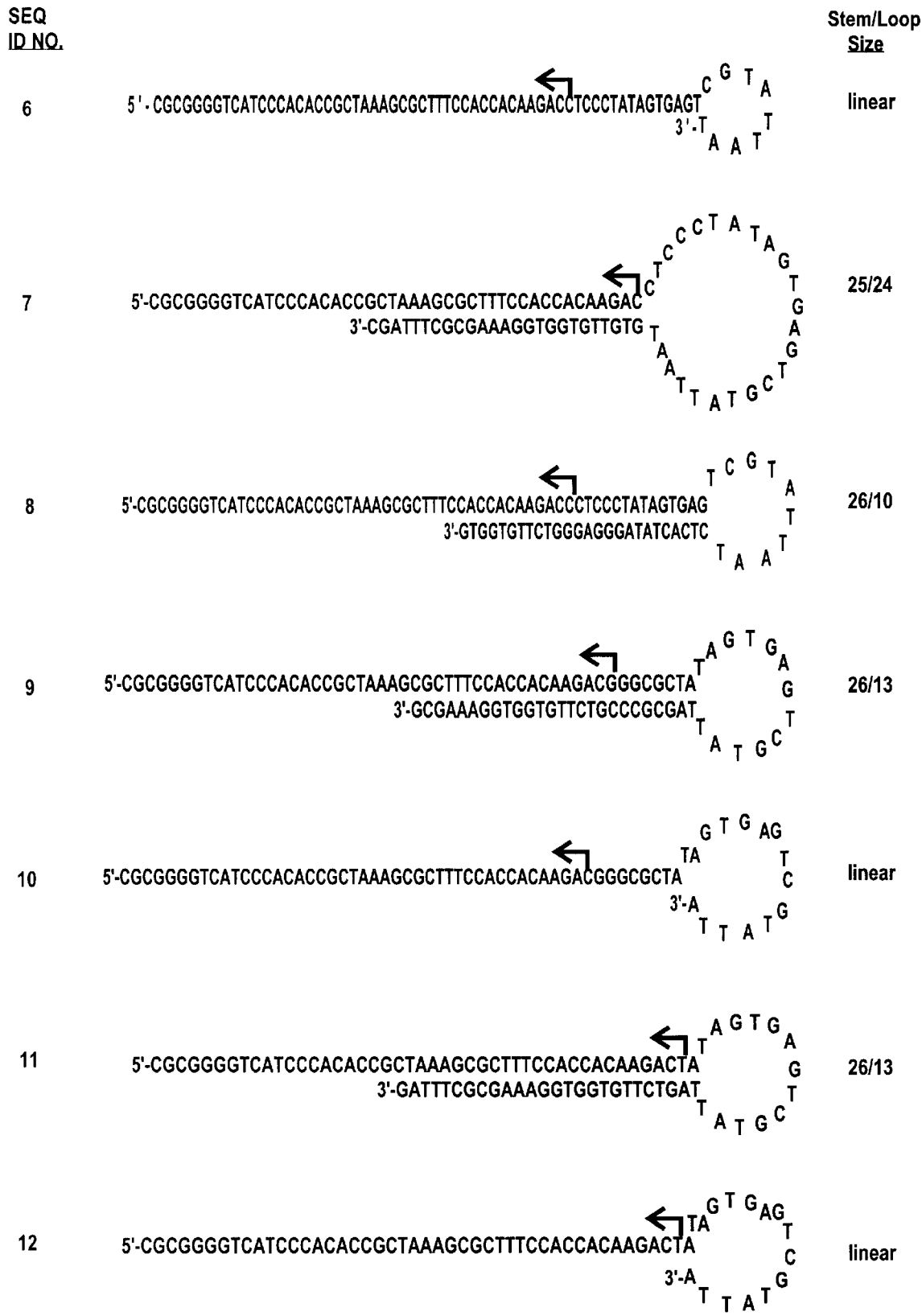
FIG. 10 provides the nucleic acid sequences, and illustrates the secondary structures, for oligonucleotides of SEQ. ID. Nos. 6–12. The arrow indicates the start site and the direction of transcription.

FIGS. 7 and 8 provide examples of target-triggered amplification using a promoter-sequestered oligonucleoside and show different possible mechanisms which can be used to achieve multiple rounds of amplification. FIG. 7, illustrates amplification using a promoter-sequestered oligonucleoside having a target-complementary region extending from its 3' end, a promoter sequence oriented to use promoter-sequestered oligonucleoside nucleic acid as a template, and using a promoter-complementary oligonucleoside. FIG. 8 illustrates a cyclic amplification process using a promoter-sequestered oligonucleoside having a target-complementary region extending from its 5' end and a promoter sequence orientated to use promoter-sequestered oligonucleoside nucleic acid as a template, and using a promoter-complementary oligonucleotide.

Referring to FIG. 7, the target-complementary region is shown having subsequences labeled a and b. The target-complementary subsequence b is joined at its 3' end to subsequence a, and is joined at its 5' end to the loop containing the promoter sequence (thick line). The loop is joined at its 5' end to the 3' end of the 5' intramolecular binding region $b_c$ which is joined to region $c_c$. The target nucleic acid is shown having region $a_c$, which is complementary to a, and region $b_c$, which is complementary to b. Step (a) shows the promoter-sequestered oligonucleoside and target nucleic acid prior to hybridization. Step (b) illustrates the promoter-sequestered oligonucleoside hybridized to the target and the formation of a double-stranded promoter region using a promoter-complementary oligonucleotide (CPS). Step (c) illustrates the production of b-c RNA transcripts. Further cycling can be carried using the promoter-sequestered oligonucleoside shown in step (a) and the transcripts shown in step (c), by $b_c$–$c_c$ now becoming the target-complementary region and b-c becoming the target sequence (e.g., see FIG. 8). FIG. 8 steps (a), (b) and (c) further illustrate cycling of RNA transcripts. Referring to FIG. 8, the target-complementary region is shown having subsequences designated $b_c$ and ($c_c$). The 3' intramolecular binding region b is joined at its 5' end to the loop containing the sequestered promoter sequence (thick line), which is joined at its 5' end to a target-complementary subsequence $b_c$ (present in the 5' intramolecular binding region), which is joined at its 5' end to the target-complementary subsequence $c_c$. The target nucleic acid is shown having region b which is complementary to $b_c$ and region c which is complementary to $c_c$. Step (a) shows the promoter-sequestered oligonucleoside and target nucleic acid prior to hybridization. Step (b) illustrates the promoter-sequestered oligonucleoside hybridized to the target and to a promoter-complementary oligonucleotide (CPS). Step (c) illustrates the production of RNA transcripts using downstream promoter-sequestered oligonucleoside nucleic acid as a template. Step (d) illustrates cycling of RNA transcripts to produce additional RNA transcripts.

V. Detection of Amplified Nucleic Acid

Amplified nucleic acid can be detected using various techniques including the use of radiolabeled nucleotide precursors and labeled detection probes. Diagnostic applications are preferably carried out using detection probes to detect amplified nucleic acid as an indication of the presence of target sequence.

Detection probes can be designed to hybridize to the amplified nucleic acid using standard techniques. If desired, or necessary, capture probes can be used to separate amplified nucleic acid from contaminants.

Capture probes involve the use of an oligonucleotide bound to a support. The bound oligonucleotide can directly or indirectly immobilize amplified nucleic acid. Direct immobilization is achieved by the amplified nucleic acid directly hybridizing to the bound oligonucleotide. Indirect immobilization is achieved by using at least one linker oligonucleotide which has two regions: (1) a region able to hybridize to the bound oligonucleotide; and (2) a region able to hybridize to the amplified nucleic acid.

Separation of the amplified product may also be useful to allow for more stringent hybridization conditions to be used during the detection step. Alternatively, or additionally, the reaction conditions may be altered using methods known to those of ordinary skill in the art in order to change (generally increase) the stringency of hybridization. For example, magnesium ion may be complexed by adding an equivalent or greater amount of ethylenediaminetetraacetic acid (EDTA) or another suitable chelator or can be bound to a chelating resin (e.g., CHELEX®, Bio-Rad Laboratories); or the ionic strength may be reduced by techniques such as dilution or by use of ion exchange.

In cases where the promoter-sequestered oligonucleoside contains sequences that may compete with the detection probe, prior removal of the promoter-sequestered oligonucleoside may be desirable. This can be achieved using various solid or liquid phase separation methods known to those of ordinary skill in the art such as through the use of a capture probe or by the use of RNase-free DNase when the competing promoter-sequestered oligonucleoside region is DNA. Alternatively, the probe may be used in amounts sufficiently in excess of those of the promoter-sequestered oligonucleoside so that competition between the probe binding site and the promoter-sequestered oligonucleoside is not significant.

EXAMPLES

Examples are provided below illustrating different aspects and embodiments of the present invention. These examples are not intended to limit the claimed invention.

Example 1
Reduction of Promoter Functioning by Formation of Loop/Stem Structures This example illustrates the ability of different promoter-sequestered oligonucleoside structures to prevent the formation of a double-stranded promoter in the absence of target sequence. Oligonucleotides of SEQ. ID. Nos. 1, 2, 3, or 4 ($1 \times 10^{-12}$ mole) in 16 μL of buffer (200 mM tris (hydroxymethyl)aminomethane-HCl (Tris-HCl) (pH 8.1), 50 mM spermidine, 25 mM dithiothrietol (DTT), 250 μg/ml bovine serum albumin (BSA), 0.05% (v/v) TRITON® X-100 non-ionic detergent, 400 mg/mL polyethylene glycol (PEG) 8000 and 100 mM $MgCl_2$) were incubated for 1 hour at 60° C. in the presence ($2.5 \times 10^{-12}$ mole) or absence of a promoter-complementary oligonucleotide (SEQ. ID. No. 20: ATTAATACGA CTCACTATAG). The samples were then treated with 2 μL of 40 mM ATP, GTP, CTP and UTP, 1 μL of RNasin (40 units) and T7 RNA Polymerase (200 units) and incubated at 37° C. for 2 hours.

After RNA polymerase-mediated amplification, the reactions were treated with 80 μL of water and 100 μL of 2×hybridization reagent (100 mM lithium succinate (pH 4.7), 2% (w/v) lithium dodecyl sulfate, 20 mM ethylenediamine tetracetic acid (EDTA), 20 mM ethylene glycol-bis (β-aminoethyl ether) N,N,N',N'-tetraacetic acid (EGTA), 15 mM Aldrithiol and 3% ethanol). The RNA polymerase-mediated amplification products were assayed using an acridinium ester (AE) labeled detection probe as described by Nelson et al., in *Nonisotopic DNA Probe Techniques*, p. 275 Academic Press, San Diego (Kricka, ed., 1992).

The detection probe, SEQ. ID. No. 21: CAGAACACCA CCTTTCGCGA AATC, was labeled with acridinium ester and was designed to specifically hybridize to a region of the predicted RNA polymerase-mediated amplification products. Ten microliters of the solution was treated with 1× hybridization reagent and incubated at 60° C. for 1 hour with 1 picomole of probe. The acridinium ester present on unhybridized probe was hydrolyzed by adding a Selection Reagent (0.15 M sodium tetraborate, pH 8.5, and 1% TRITONO® X-100 non-ionic detergent) and heating the sample to 60° C. for 9 minutes. Chemiluminescence was measured in a luminometer by injection of 0.1% $H_2O_2$ in 4 mM $HNO_3$ immediately followed by 1 N NaOH.

The results are shown in Table 1. The data illustrates transcription in the presence or absence of a promoter-complementary oligonucleotide. In both cases different promoter-sequestered oligonucleoside structures affected amplification.

TABLE I

| CPS | SEQ. ID. NO. 1 | SEQ. ID. NO. 2 | SEQ. ID. NO. 3 | SEQ. ID. NO. 4 |
|---|---|---|---|---|
| − | 20,566 | 29,965 | 33,560 | 11,913 |
| + | 699,493 | 184,894 | 361,109 | 45,834 |
| Structure | linear | 24/24 | 21/15 | 26/10 |

"CPS" refers to the promoter-complementary oligonucleotide. The data is shown as measured RLU values. "Structure" refers to the number of bases in the double-stranded stem over the number of bases in the loop. SEQ. ID. NO. 1 has a linear structure and, thus, does not contain a sequestered promoter.

In comparing the results obtained when using different oligonucleosides, those oligonucleosides having the same initiation sequences should be compared with each other. SEQ. ID. Nos. 1, 2, 3, and 4 all have the same initiation sequence. The data shown in Table I demonstrates that a decrease in RNA polymerase activity can be achieved when the promoter is sequestered by smaller loop regions in the absence of target.

Oligonucleotides of SEQ. ID. Nos. 6, 7, 9, 10, 11 and 12 were also tested as described above, except 1 picomole of AE-labeled probe SEQ. ID. No. 22: CTAAAGCGCT TTC-CACCACA AGAC was used to detect RNA polymerase-mediated amplification products, and the hydrolysis reaction lasted 10 minutes. SEQ. ID. Nos. 6 and 7 have same initiation sequence, SEQ. ID. Nos. 9 and 10 have the same initiation sequence, and SEQ. ID. Nos. 11 and 12 have the same initiation sequence.

The effect of promoter sequestration upon promoter function is shown in Table II.

TABLE II

| CPS | Exp. | Oligonucleotide (SEQ. ID. No.) | | | | | |
|---|---|---|---|---|---|---|---|
| | | 6 | 7 | 9 | 10 | 11 | 12 |
| − | 1 | 5,623 | 13,956 | 1,076 | 8,628 | 1,109 | 4,046 |
| | 2 | 14,423 | 7,596 | 1,744 | 7,932 | 3,933 | 4,619 |
| | Ave. | 10,023 | 10,776 | 1,410 | 8,280 | 2,521 | 4,333 |
| + | 1 | 1,140,520 | 743,698 | 5,389 | 410,139 | 9,112 | 354,260 |
| | 2 | 568,309 | 419,044 | 10,177 | 429,199 | 7,431 | 78,447 |
| | Ave. | 854,415 | 581,371 | 7,783 | 419,669 | 8,272 | 216,354 |
| Structure | | linear | 25/24 | 26/13 | linear | 26/13 | linear |

The data is shown as measured RLU values.

The results shown in Table II demonstrate that the trends in Table I are not restricted to a particular target binding region or initiation sequences.

Example 2
Effect of Using Sequestered Complementary Promoters Compared to Unsequestered Complementary Promoters This example further illustrates the ability of different promoter-sequestered oligonucleoside structures to prevent the formation of a double-stranded promoter in the absence of target sequence. Oligonucleotides of SEQ. ID. Nos. 6, 7, 9, and 10 were subjected to the same RNA polymerase-mediated amplification conditions described in Example 1, and promoter-complementary oligonucleotides SEQ. ID. Nos. 13–19 were used to transcribe the target. RNA polymerase-mediated amplification products were analyzed using an acridinium ester labeled oligonucleotide as described above in the second set of experiments of Example 1. The results are shown in Table III.

TABLE III

| CPS | Promoter-Sequestered SEQ. ID. No. | | | |
|---|---|---|---|---|
| SEQ. ID. NO. | 6 | 7 | 9 | 10 |
| T7 | 595,126 | 109,609 | 17,143 | 596,905 |
| 13 | 21,181 | 5,680 | 4,004 | 38,610 |
| 14 | 402,860 | 13,469 | 5,198 | 190,229 |
| 15 | 16,605 | 3,960 | 3,692 | 88,068 |
| 16 | 378,534 | 24,521 | 6,952 | 314,827 |
| 17 | 7,469 | 2,454 | 2,185 | 24,700 |
| 18 | 12,754 | 2,681 | 3,340 | 19,004 |
| 19 | 135,519 | 15,007 | 4,093 | 85,249 |
| Structure | linear | sequestered | sequestered | linear |

T7 refers to a T7 polymerase sequence. The data is shown as measured RLU values.

The results show that less transcription is obtained using promoter-complementary oligonucleotides, themselves having a stem-loop structure, compared to that obtained with unsequestered promoter-complementary oligonucleotides. The results also show that a reduction in activity may be even more pronounced when a stem-loop promoter-complementary oligonucleotide is combined with a promoter-sequestered oligonucleoside.

Example 3
Hybridization of Promoter-Sequestered Oliconucleosides to Their Target at Different Temperatures This example illustrates the ability of a $^{32}$P-labeled target nucleic acid sequence to hybridize to promoter-sequestered oligonucleosides at different temperatures. An RNA target of SEQ. ID. No. 23: GUCUUGUGGU GGAAAGCGCU UUAGCGGUGU GGGAUGACCC CGCG, was chemically synthesized. The RNA target was radioactively labeled by combining 13 picomoles (1 µL) of the target with 5 µL of [γ-$^{32}$P] ATP (3,000 Ci/mmole, 10 mM), 1 µL of T4 polynucleotide kinase (10 units), and 2 µL of kinase buffer (500 mM Tris-HCl, pH 8.0, 100 MM MgCl$_2$, 50 mM DTT, 1.0 mM EDTA and 1.0 mM spermidine), and 11 µL of water, and incubating the solution at 37° C. for 1.5 hours. After labeling, the solution was treated with 5 µL of 0.5 M EDTA, 200 µL of 5 M NH$_4$OAc, 2 µL of 40 µg/µL of bovine serum albumin (BSA) and 800 µL of ethanol. The solution was cooled to −78° C. for 10 minutes, then the labeled RNA pelleted by centrifugation. The supernatant was discarded and the pellet dissolved in 100 µL water.

$^{32}$P-labeled RNA (100 femtomole) was combined with 1 picomole of oligonucleotides SEQ. ID. NOs. 6, 8, 11, or 12 in 20 µL of transcription buffer (see Example 1) and heated to 37° C., 60° C., or 75° C. for 1 hour. The hybridized samples were treated with 5 µL of non-denaturing loading buffer (40% sucrose, 0.25% xylene cyanol and 0.25% bromophenol blue). Fifteen microliters of each of the resulting solutions were loaded onto a 10% non-denaturing polyacrylamide gel in 1×0.045 M Tris-borate, 1 mM EDTA (pH 8.0) (TBE). Electrophoresis was performed at 9 W, 23 mA, and 750 V. The gel was then exposed to x-ray film for about 4 to about 16 hours, intensifying screens were used, and the film was developed.

Hybridization of the promoter-sequestered oligonucleosides to the labeled RNA target was observed as reduced mobility of labeled RNA through the non-denaturing gel. Bands indicating the formation of double-stranded hybrids were observed at all three temperatures. The ability to form a hybrid at 37° C. is useful for carrying out multiple rounds of amplification at an essentially constant temperature under conditions in which both hybridization and RNA polymerase mediated amplification occurs.

The RNA target showed increasing degradation with increasing temperature, thus binding of target to promoter-sequestered oligonucleoside was reduced. Binding of target to promoter-sequestered oligonucleosides SEQ. ID. Nos. 6, 8, 11 and 12, was nearly quantitative as evidenced by the disappearance of the target band.

Example 4
Oligonucleoside:Target Hybridization

This example further illustrates the ability of a promoter-sequestered oligonucleoside to hybridize to a specific target. The experiment was carried out using two different protocols. In one protocol, one picomole of promoter-sequestered oligonucleosides SEQ. ID. Nos. 6, 7, 8, 11 or 12 was combined with 100 femtomole of $^{32}$P labeled RNA target oligonucleotide SEQ. ID. No. 23 in 20 µL of transcription buffer. In another protocol 100 femtomoles of $^{32}$P labeled promoter-sequestered oligonucleoside was combined with 1 picomole of unlabeled RNA target oligonucleotide SEQ. ID. No. 23 in 20 µL of transcription buffer. In both protocols, the samples were then incubated at 60° C. for 1 hour and then treated with 5 µL of non-denaturing loading buffer (see, Example 3). Ten microliters of each sample were loaded onto a non-denaturing polyacrylamide gel and subjected to electrophoresis as described in Example 3.

The autoradiogram showed co-migrating labeled bands having the same size regardless of whether the label is on the promoter-sequestered oligonucleoside or the target suggesting they are in same species, the hybridized duplex. Hybridization appeared to be very efficient under these conditions.

Example 5
Target-Triggered Amplification

This example illustrates the use of different promoter-sequestered oligonucleosides to achieve target-triggered amplification. One femtomole of oligonucleotide SEQ. ID. Nos. 6, 7, 8, 9, 10, 11, or 12, was combined with 100 femtomole of promoter-complementary oligonucleoside in transcription buffer in the presence or absence of 10 femtomole of target nucleic acid SEQ. ID. No. 23. The oligonucleotides were subjected to the RNA polymerase mediated amplification conditions described in Example 1. The production of RNA transcripts were measured using an AE-labeled probe as described in Example 1.

Table V, provides data illustrating amplification in the presence and absence of target.

TABLE V

| SEQ. ID. NO. | −Target | +Target | Structure |
|---|---|---|---|
| 6 | 1,347,325 | 973,434 | linear |
| 7 | 878,036 | 357,302 | 25/24 |
| 8 | 44,262 | 173,511 | 26/10 |
| 9 | 11,226 | 18,806 | 26/13 |
| 10 | 681,339 | 667,722 | linear |
| 11 | 8,518 | 46,624 | 26/13 |
| 12 | 123,156 | 143,453 | linear |

The data is shown as measured RLU values.

No significant enhancement of RNA polymerase mediated amplification in the presence of target sequence was observed with linear oligonucleotides of SEQ. ID. Nos. 6, 10 and 12. Significant enhancement of RNA polymerase mediated amplification in the presence of target sequence was observed for promoter-sequestered oligonucleosides of SEQ. ID. Nos. 8, 9 and 11. Promoter-sequestered oligonucleosides of SEQ. ID. Nos. 8 and 11 showed several fold (about 4 to 5.5 fold) increased RNA polymerase mediated amplification.

Other embodiments are within the following claims. Thus, while several embodiments have been shown and described, various modifications may be made, without departing from the spirit and scope of the present invention.

SEQUENCE LISTING (1) GENERAL INFORMATION:

(iii) NUMBER OF SEQUENCES:   23

(2) INFORMATION FOR SEQ ID NO:   1:

(i) SEQUENCE CHARACTERISTICS:
       (A) LENGTH:        73 base pairs
       (B) TYPE:          nucleic acid
       (C) STRANDEDNESS:  single
       (D) TOPOLOGY:     linear (ii) SEQUENCE DESCRIPTION: SEQ ID NO: 1:

GTACAGAACA CCACCTTTCG CGAAATCGCC ACACCCTACT GGGGCGCCTC      50

CCTATAGTGA GTCGTGTATT AAT      73

(2) INFORMATION FOR SEQ ID NO:   2:

(i) SEQUENCE CHARACTERISTICS:
       (A) LENGTH:        97 base pairs
       (B) TYPE:          nucleic acid
       (C) STRANDEDNESS:  single
       (D) TOPOLOGY:     linear (ii) SEQUENCE DESCRIPTION: SEQ ID NO: 2:

GTACAGAACA CCACCTTTCG CGAAATCGCC ACACCCTACT GGGGCGCCTC        50

CCTATAGTGA GTCGTGTATT AATGCGCCCC AGTAGGGTGT GGCGATT          97

(2) INFORMATION FOR SEQ ID NO:   3:

(i) SEQUENCE CHARACTERISTICS:
      (A) LENGTH:         94 base pairs
      (B) TYPE:           nucleic acid
      (C) STRANDEDNESS:   single
      (D) TOPOLOGY:       linear (ii) SEQUENCE DESCRIPTION: SEQ ID NO: 3:

GTACAGAACA CCACCTTTCG CGAAATCGCC ACACCCTACT GGGGCGCCTC        50

CCTATAGTGA GTCGTGTATT AATTATAGGG AGGCGCCCCA GTAG              94

(2) INFORMATION FOR SEQ ID NO:   4:

(i) SEQUENCE CHARACTERISTICS:
      (A) LENGTH:         97 base pairs
      (B) TYPE:           nucleic acid
      (C) STRANDEDNESS:   single
      (D) TOPOLOGY:       linear (ii) SEQUENCE DESCRIPTION: SEQ ID NO: 4:

GTACAGAACA CCACCTTTCG CGAAATCGCC ACACCCTACT GGGGCGCCTC        50

CCTATAGTGA GTCGTATTAA TCTCACTATA GGGAGGCGCC CCAGTAG           97

(2) INFORMATION FOR SEQ ID NO:   5:

(i) SEQUENCE CHARACTERISTICS:
      (A) LENGTH:         88 base pairs
      (B) TYPE:           nucleic acid
      (C) STRANDEDNESS:   single
      (D) TOPOLOGY:       linear (ii) SEQUENCE DESCRIPTION: SEQ ID NO: 5:

GTACAGAACA CCACCTTTCG CGAAATCGCC ACACCCTACT GGGGCGCTAT        50

AGTGAGTCGT ATTAGCGCCC CAGTAGGGTG TGGCGATT                     88

(2) INFORMATION FOR SEQ ID NO:   6:

(i) SEQUENCE CHARACTERISTICS:
      (A) LENGTH:         68 base pairs
      (B) TYPE:           nucleic acid
      (C) STRANDEDNESS:   single
      (D) TOPOLOGY:       linear (ii) SEQUENCE DESCRIPTION: SEQ ID NO: 6:

CGCGGGGTCA TCCCACACCG CTAAAGCGCT TTCCACCACA AGACCTCCCT        50

ATAGTGAGTC GTATTAAT                                           68

(2) INFORMATION FOR SEQ ID NO:   7:

(i) SEQUENCE CHARACTERISTICS:
      (A) LENGTH:         93 base pairs
      (B) TYPE:           nucleic acid
      (C) STRANDEDNESS:   single
      (D) TOPOLOGY:       linear (ii) SEQUENCE DESCRIPTION: SEQ ID NO: 7:

CGCGGGGTCA TCCCACACCG CTAAAGCGCT TCCACCACA AGACCTCCCT         50

```
ATAGTGAGTC GTATTAATGT GTTGTGGTGG AAAGCGCTTT AGC                    93
```

(2) INFORMATION FOR SEQ ID NO: 8:

(i) SEQUENCE CHARACTERISTICS:
        (A) LENGTH:       95 base pairs
        (B) TYPE:         nucleic acid
        (C) STRANDEDNESS:  single
        (D) TOPOLOGY:     linear (ii) SEQUENCE DESCRIPTION: SEQ ID NO: 8:

```
CGCGGGGTCA TCCCACACCG CTAAAGCGCT TTCCACCACA AGACCCTCCC            50

TATAGTGAGT CGTATTAATC TCACTATAGG GAGGGTCTTG TGGTG                 95
```

(2) INFORMATION FOR SEQ ID NO: 9:

(i) SEQUENCE CHARACTERISTICS:
        (A) LENGTH:       91 base pairs
        (B) TYPE:         nucleic acid
        (C) STRANDEDNESS:  single
        (D) TOPOLOGY:     linear (ii) SEQUENCE DESCRIPTION: SEQ ID NO: 9:

```
CGCGGGGTCA TCCCACACCG CTAAAGCGCT TTCCACCACA AGACGGGCGC            50

TATAGTGAGT CGTATTAGCG CCCGTCTTGT GGTGGAAAGC G                     91
```

(2) INFORMATION FOR SEQ ID NO: 10:

(i) SEQUENCE CHARACTERISTICS:
        (A) LENGTH:       67 base pairs
        (B) TYPE:         nucleic acid
        (C) STRANDEDNESS:  single
        (D) TOPOLOGY:     linear (ii) SEQUENCE DESCRIPTION: SEQ ID NO: 10:

```
CGCGGGGTCA TCCCACACCG CTAAAGCGCT TTCCACCACA AGACGGGCGC            50

TATAGTGAGT CGTATTA                                                67
```

(2) INFORMATION FOR SEQ ID NO: 11:

(i) SEQUENCE CHARACTERISTICS:
        (A) LENGTH:       85 base pairs
        (B) TYPE:         nucleic acid
        (C) STRANDEDNESS:  single
        (D) TOPOLOGY:     linear (ii) SEQUENCE DESCRIPTION: SEQ ID NO: 11:

```
CGCGGGGTCA TCCCACACCG CTAAAGCGCT TTCCACCACA AGACTATAGT            50

GAGTCGTATT AGTCTTGTGG TGGAAAGCGC TTTAG                            85
```

(2) INFORMATION FOR SEQ ID NO: 12:

(i) SEQUENCE CHARACTERISTICS:
        (A) LENGTH:       64 base pairs
        (B) TYPE:         nucleic acid
        (C) STRANDEDNESS:  single
        (D) TOPOLOGY:     linear (ii) SEQUENCE DESCRIPTION: SEQ ID NO: 12:

```
CGCGGGGTCA TCCCACACCG CTAAAGCGCT TTCCACCACC ACAAGACTAT            50

AGTGAGTCGT ATTA                                                   64
```

```
(2) INFORMATION FOR SEQ ID NO:    13:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (ii) SEQUENCE DESCRIPTION: SEQ ID NO: 13:

ATTAATACGA CTCACTATAG AGTGAGTCGT ATTAAT                                    36

(2) INFORMATION FOR SEQ ID NO:    14:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (ii) SEQUENCE DESCRIPTION: SEQ ID NO: 14:

ATTAATACGA CTCACTATAG GTATAGTCGT GCTATA                                    36

(2) INFORMATION FOR SEQ ID NO:    15:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (ii) SEQUENCE DESCRIPTION: SEQ ID NO: 15:

CTATAGTGAG TCGTATATTA ATACGACTCA CTATAG                                    36

(2) INFORMATION FOR SEQ ID NO:    16:

(i) SEQUENCE CHARACTERISTICS:
        (A) LENGTH:            36 base pairs
        (B) TYPE:              nucleic acid
        (C) STRANDEDNESS:      single
        (D) TOPOLOGY:          linear (ii) SEQUENCE DESCRIPTION: SEQ ID NO: 16:

ATATCGTGCT GATATGATTA ATACGACTCA CTATAG                                    36

(2) INFORMATION FOR SEQ ID NO:    17:

(i) SEQUENCE CHARACTERISTICS:
        (A) LENGTH:            39 base pairs
        (B) TYPE:              nucleic acid
        (C) STRANDEDNESS:      single
        (D) TOPOLOGY:          linear (ii) SEQUENCE DESCRIPTION: SEQ ID NO: 17:

GACCTATAGT GAGTCGATTA ATACGACTCA CTATAGGTC                                 39

(2) INFORMATION FOR SEQ ID NO:    18:

(i) SEQUENCE CHARACTERISTICS:
        (A) LENGTH:            41 base pairs
        (B) TYPE:              nucleic acid
        (C) STRANDEDNESS:      single
        (D) TOPOLOGY:          linear (ii) SEQUENCE DESCRIPTION: SEQ ID NO: 18:

AAGACCTATA GTGAGTATTA ATACGACTCA CTATAGGTCT T                              41
```

(2) INFORMATION FOR SEQ ID NO: 19:

(i) SEQUENCE CHARACTERISTICS:
       (A) LENGTH:        46 base pairs
       (B) TYPE:          nucleic acid
       (C) STRANDEDNESS:  single
       (D) TOPOLOGY:      linear (ii) SEQUENCE DESCRIPTION: SEQ ID NO: 19:

CCACCACAAG ACCTATTAAT ACGACTCACT ATAGGTCTTG TGGTGG                                46

(2) INFORMATION FOR SEQ ID NO: 20:

(i) SEQUENCE CHARACTERISTICS:
       (A) LENGTH:        20 base pairs
       (B) TYPE:          nucleic acid
       (C) STRANDEDNESS:  single
       (D) TOPOLOGY:      linear (ii) SEQUENCE DESCRIPTION: SEQ ID NO: 20:

ATTAATACGA CTCACTATAG                                                            20

(2) INFORMATION FOR SEQ ID NO: 21:

(i) SEQUENCE CHARACTERISTICS:
       (A) LENGTH:        24 base pairs
       (B) TYPE:          nucleic acid
       (C) STRANDEDNESS:  single
       (D) TOPOLOGY:      linear (ii) SEQUENCE DESCRIPTION: SEQ ID NO: 21:

CAGAACACCA CCTTTCGCGA AATC                                                       24

(2) INFORMATION FOR SEQ ID NO: 22:

(i) SEQUENCE CHARACTERISTICS:
       (A) LENGTH:        24 base pairs
       (B) TYPE:          nucleic acid
       (C) STRANDEDNESS:  single
       (D) TOPOLOGY:      linear (ii) SEQUENCE DESCRIPTION: SEQ ID NO: 22:

CTAAAGCGCT TTCCACCACA AGAC                                                       24

(2) INFORMATION FOR SEQ ID NO: 23:

(i) SEQUENCE CHARACTERISTICS:
       (A) LENGTH:        44 base pairs
       (B) TYPE:          nucleic acid
       (C) STRANDEDNESS:  single
       (D) TOPOLOGY:      linear (ii) SEQUENCE DESCRIPTION: SEQ ID NO: 23:

GUCUUGUGGU GGAAAGCGCU UUAGCGGUGU GGGAUGACCC CGCG                                 44

We claim:

1. A promoter-sequestered oligonucleoside comprising:
   a) a stem comprising a first nucleic acid sequence located 3' of a loop region and a second nucleic acid sequence located 5' of said loop region,
      wherein said first nucleic acid sequence and said second nucleic acid sequence are able to form an intramolecular hybrid with each other, provided that either said first nucleic acid sequence or said second nucleic acid sequence comprises at least a portion of a target-complementary nucleic acid region that can hybridize to a target sequence under amplifying conditions, thereby increasing the accessibility of an RNA polymerase promoter sequence, of which all or a portion is located within said loop region, for hybridization with a promoter-complementary oligonucleotide under said conditions; and
   b) a single-stranded loop region located between said first nucleic acid sequence and said second nucleic acid sequence,
      wherein said portion of said promoter sequence located within said single-stranded loop region is sufficient such that said promoter sequence contains less than 40% of activity of said promoter sequence when said promoter sequence is double-stranded; and wherein said oligonucleoside consists of deoxyribonucleotides, 2-methoxyribonucleotides, ribonucleotides, or a combination thereof.

2. The oligonucleoside of claim 1, wherein said first nucleic acid sequence comprises at least said portion of said target-complementary nucleic acid region, and said target-complementary nucleic acid region further comprises a nucleic acid sequence extending from said first nucleic acid sequence 3' of said stem.

3. The oligonucleoside of claim 2, wherein said promoter sequence is oriented to produce RNA transcripts using a nucleoside sequence region present in said promoter-swquestered oligonucleoside as a template.

4. The oligonucleoside of claim 2, wherein said promoter sequence is oriented to produce RNA transcripts using said target sequence as a template.

5. The oligonucleoside of claim 1, wherein said second nucleic acid sequence comprises at least said portion of said target-complementary nucleic acid region, and said target-complementary nucleic acid region further comprises a nucleic acid sequence extending from said second nucleic acid sequence 5' of said stem.

6. The oligonucleoside of claim 5, wherein said promoter sequence is oriented to produce RNA transcripts using nucleic acid present in said promoter-sequestered oligonucleoside as a template.

7. A promoter-sequestered oligonucleoside comprising:

a nucleic acid 3' intramolecular binding region, a single-stranded loop region comprising all, or a portion of, an RNA polymerase promoter sequence, wherein said loop region is located 5' to said 3' intramolecular binding sequence, and a nucleic acid 5' intramolecular binding region located 5' to said loop region, wherein either said 3' intramolecular binding region or said 5' intramolecular binding region comprises a first target-complementary sequence, provided that it said 3' intramolecular binding region comprises said first target-complementary sequence then a second target-complementary sequence located 3' of said first target-complementary sequence is present and if said 5' intramolecular binding region comprises said first target-complementary sequence then a second target-complementary sequence located 5' of said first target-complementary sequence is present, wherein under RNA polymerase mediated amplification conditions, when a target sequence is absent, said 3' intramolecular binding region and said 5' intramolecular binding region form an intramolecular hybrid, thereby inhibiting hybridization of said promoter sequence with a promoter-complementary oligonucleotide, and, when said target sequence is present, said promoter sequence becomes more accessible for hybridization with said promoter-complementary oligonucleotide.

8. The oligonucleoside of claim 7, wherein said oligonucleoside consists of deoxyribonucleotides, 2-methoxyribonucleotides, or a combination thereof.

9. The oligonucleoside of claim 7, wherein said promoter sequence is oriented to produce RNA transcripts using a nucleic acid sequence present in said promoter-sequestered oligonucleoside as a template.

10. The oligonucleoside of claim 7, wherein said 3' intramolecular binding region is said first target-complementary sequence.

11. The oligonucleoside of claim 10, further comprising a target non-complementary sequence located 3' of said second target-complementary sequence.

12. The oligonucleoside of claim 7, wherein said 5' intramolecular binding region comprises said first target-complementary sequence.

13. The oligonucleoside of claim 12, further comprising a target non-complementary region located 5' of said second target-complementary sequence.

14. A method for triggering amplification of a nucleic acid sequence in the presence of a target sequence comprising the steps of:

a) combining under amplifying conditions compatible with RNA polymerase mediated amplification:

a promoter-sequestered oligonucleoside comprising:

a stem comprising a first nucleic acid sequence and a second nucleic acid sequence, wherein said first nucleic acid sequence and second nucleic acid sequence are able to form an intramolecular hybrid under said amplifing conditions, wherein either said first nucleic acid sequence or said second nucleic acid sequence comprises at least a part of a target-complementary nucleic acid sequence region, a single-stranded loop region located between said first nucleic acid sequence and said second nucleic acid sequence, wherein said first nucleic acid sequence is 3' of said loop reqion and said second nucleic acid sequence is 5' of said loop region, a sequestered RNA polymerase promoter sequence of which all, or a portion, is located within said loop region, wherein said target-complementary nucleic acid sequence hybridizes to said target sequence under said amplifying conditions such that said promoter sequence becomes more accessible for hybridization with a complementary oligonucleotide under said conditions; and a sample comprising said target sequence, b) forming a functional double-stranded promoter region, and c) producing multiple copies of RNA transcripts using said targret sequence or said target-complementary sequence as a template under said amplifying conditons.

15. The method of claim 14, wherein said portion of said promoter sequence located within said loop region is sufficient such that said promoter sequence contains less than 40% of activity of said promoter sequence when made double-stranded, said first nucleic acid sequence comprises said part of said target-complementary region, and said target-complementary region further comprises a nucleic acid sequence extending from said first nucleic acid sequence 3' of said stem.

16. The method of claim 14, wherein said portion of said promoter sequence located within said loop region is sufficient such that said promoter sequence contains less than 40% of activity of said promoter sequence when said promoter is double-stranded, said second nucleic acid sequence comprises said part of said target-complementary region, and said target-complementary region further comprises a nucleic acid sequence extending from second nucleic acid sequence 5' of said stem.

17. The method of claim 14, wherein said step (b) comprises providing a promoter-complementary oligonucleotide, wherein said promoter-complementary oligonucleotide hybridizes to said promoter sequence to form said double-stranded promoter.

18. The method of claim 14, wherein said step (b) comprises providing an oligonucleotide primer which hybridizes to said promoter-sequestered oligonucleoside 3' of the 5' end of said promoter sequence, and extending the 3' end of said oligonucleotide primer to produce said functional double-stranded promoter.

19. The method of claim 14, wherein said target sequence is RNA and said promoter-sequestered oligonucleoside consists of deoxyribonucleotides, 2-methoxyribonucleotides, ribonucleotides, or a combination thereof.

20. The method of claim 14, wherein RNA transcripts produced from said step (c) are further amplified by repeating said steps (a), (b) and (c).

21. The method of claim 14, wherein said amplifying conditions are isothermal transcription mediated amplification conditions.

22. The method of claim 14, wherein said oligonucleoside further comprises a target non-complementary sequence located 5' of said stem which is amplified during said step (c).

23. A method for detecting whether a target nucleic acid sequence is present in a sample comprising the steps of:
   a) combining under amplifying conditions compatible with RNA polymerase mediated amplification:
      a promoter-sequestered oligonucleoside comprising:
         a stem comprising a first nucleic acid sequence and a second nucleic acid sequence, wherein said first nucleic acid sequence and said second nucleic acid sequence are able to form an intramolecular hybrid under said amplifying conditions, wherein either said first nucleic acid sequence or said second nucleic acid sequence comprises at least a part of a target-complementary nucleic acid sequence region,
         a single-stranded loop region located between said first nucleic acid sequence and second nucleic acid sequence, said first nucleic acid sequence being 3' of said loop region and said second nucleic acid sequence being 5' of said loop region,
         a sequestered RNA polymerase promoter sequence, of which all, or a portion, of said promoter sequence is located within said loop region,
         wherein said target-complementary nucleic acid sequence region hybridizes to said target nucleic acid sequence under said amplifying conditions such that said promoter sequence becomes more accessible for hybridization with a promoter-complementary oligonucleotide under said amplifying conditions; and
      said sample,
   b) forming a functional double-stranded promoter region when said target nucleic acid sequence is present in said sample,
   c) producing RNA transcripts under said amplifying conditions using said functional promoter region produced in step (b), and
   d) detecting whether RNA transcripts are produced in step (c).

24. The method of claim 23, wherein said portion of said promoter sequence located within said loop region is sufficient such that said promoter sequence contains less than 40% of activity of said promoter sequence when said promoter sequence is double-stranded, said first nucleic acid is said part of said target-complementary sequence region, and said target-complementary sequence region further comprises a sequence extending 3' of said first nucleic acid.

25. The method of claim 23, wherein said portion of said promoter sequence located within said loop region is sufficient such that said promoter sequence contains less than 40% of activity of said promoter sequence when said promoter sequence is double-stranded, said second nucleic acid is said part of said target-complementary sequence region, and said target-complementary sequence region further comprises a sequence extending 5' of said second nucleic acid.

26. The method claim 23, wherein said oligonucleoside further comprises a 5' target non-complementary reporter sequence which is amplified and detected if said target nucleic acid sequence is present.

27. The method of claim 24, wherein one or more RNA transcripts from said step (c) is further amplified by repeating said steps (a), (b) and (c).

28. The method of claim 25, wherein one or more RNA transcripts from said step (c) is further amplified by repeating said steps (a), (b) and (c).

29. The method of claim 23, wherein said target nucleic acid sequence is RNA and said promoter-sequestered oligonucleoside consists of deoxyribonucleotides, 2-methoxyribonucleotides, ribonucleotides, or a combination thereof.

30. The oligonucleoside of claim 1, further comprising a blocking moiety at a 3' end of said oligonucleoside, wherein said blocking moiety is capable of preventing primer extension of said oligonucleoside.

31. The oligonucleoside of claim 1, wherein said RNA polymerase promoter sequence is located completely within said single-stranded loop region.

32. The oligonucleoside of claim 1, wherein said first nucleic acid sequence is hybridized to said second nucleic acid sequence.

33. The oligonucleoside of claim 1, wherein said first nucleic acid sequence is perfectly complementary to said second nucleic acid sequence.

34. The oligonucleoside of claim 7, wherein the 3' intramolecular binding region further comprises a 3' blocking moiety capable of preventing primer extension of said oligonucleoside.

35. The method of claim 14, wherein the promoter-sequestered oligonucleoside of step a) further comprises a blocking moiety at a 3' end of said first nucleic acid sequence, wherein said blocking moiety is capable of preventing primer extension of said oligonucleoside.

36. The method of claim 23, wherein the promoter-sequestered oligonucleoside of step a) further comprises a blocking moiety at a 3' end of said first nucleic acid sequence, wherein said blocking moiety is capable of preventing primer extension of said oligonucleoside.

37. The method of claim 23, wherein the promoter-sequestered oligonucleoside of step a) comprises an RNA polymerase promoter sequence located completely within said loop region.

* * * * *

UNITED STATES PATENT AND TRADEMARK OFFICE
CERTIFICATE OF CORRECTION

PATENT NO. : 6,025,133
DATED : FEBRUARY 15, 2000
INVENTOR(S) : Stull *et al.*

It is certified that error appears in the above-identified patent and that said Letters Patent is hereby corrected as shown below:

In Claim 1, Column 31, line 15, replace "swquestered" with --sequestered--;

In Claim 7, Column 31, line 39, replace "it" with --if--; and

In Claim 14, Column 32, line 28, replace "reqion" with --region--.

Signed and Sealed this

Twenty-seventh Day of February, 2001

Attest:

NICHOLAS P. GODICI

Attesting Officer

Acting Director of the United States Patent and Trademark Office